US008637075B2

(12) United States Patent
Pedersen et al.

(10) Patent No.: US 8,637,075 B2
(45) Date of Patent: Jan. 28, 2014

(54) COLOSTRUM COMPOSITION

(75) Inventors: Ninfa Rangel Pedersen, Aalborg SØ (DK); Steen Palle, Vadum (DK)

(73) Assignee: Pharma GP ApS, Naestved (DK)

( * ) Notice: Subject to any disclaimer, the term of this patent is extended or adjusted under 35 U.S.C. 154(b) by 0 days.

(21) Appl. No.: 13/063,617

(22) PCT Filed: Sep. 10, 2009

(86) PCT No.: PCT/DK2009/050234
§ 371 (c)(1),
(2), (4) Date: Nov. 3, 2011

(87) PCT Pub. No.: WO2010/028652
PCT Pub. Date: Mar. 18, 2010

(65) Prior Publication Data
US 2012/0039950 A1 Feb. 16, 2012

Related U.S. Application Data

(60) Provisional application No. 61/105,507, filed on Oct. 15, 2008.

(30) Foreign Application Priority Data

Sep. 12, 2008 (DK) ................................ 2008 01286

(51) Int. Cl.
*A61K 38/17* (2006.01)
*A61K 9/48* (2006.01)

(52) U.S. Cl.
USPC .............................. 424/452; 435/456; 514/12

(58) Field of Classification Search
USPC ........................................ 424/400
See application file for complete search history.

(56) References Cited

U.S. PATENT DOCUMENTS

| 4,588,580 | A | 5/1986 | Gale et al. | |
|---|---|---|---|---|
| 4,788,062 | A | 11/1988 | Gale et al. | |
| 4,904,475 | A | 2/1990 | Gale et al. | |
| 4,927,408 | A | 5/1990 | Haak et al. | |
| 6,844,014 | B1 | 1/2005 | Rafkin | |
| 6,939,847 | B2 | 9/2005 | Stanton et al. | |
| 2003/0003059 | A1* | 1/2003 | Dana ............................... | 424/49 |
| 2005/0130261 | A1 | 6/2005 | Wils et al. | |
| 2005/0147664 | A1* | 7/2005 | Liversidge et al. ........... | 424/452 |
| 2007/0065399 | A1 | 3/2007 | Boldogh et al. | |
| 2007/0110758 | A1 | 5/2007 | Campbell et al. | |
| 2007/0142292 | A1* | 6/2007 | Varadhachary et al. ........ | 514/12 |

FOREIGN PATENT DOCUMENTS

| EP | 1 894 943 A2 | 3/2008 |
|---|---|---|
| WO | WO 02/38123 A1 | 5/2002 |
| WO | WO 2007/000651 A1 | 1/2007 |
| WO | WO 2007/009790 A1 | 1/2007 |
| WO | WO 2007/039124 A2 | 4/2007 |
| WO | WO 2007/112716 A1 | 10/2007 |
| WO | WO 2007/112717 A1 | 10/2007 |

OTHER PUBLICATIONS

Averbeck, Marco et al., "Differential Regulation of Hyaluronan Metabolism in the Epidermal and Dermal Compartments of Human Skin by UVB Irradiation" Journal of Investigative Dermatology, 2007, pp. 687-697, vol. 127.
Block, Allan et al., "Water Vapor Sorption of Hyaluronic Acid" Biochim. Biophys. Acta, 1970, pp. 69-75, vol. 201.
Coo-Ranger, Jill J. et al., "Ionic Silicone surfactants in Water-In-Silicone Oil Emulsions Containing Proteins" Polymer Preprints, 2004, pp. 674-675, vol. 45.
Davis, J.M., et al., "Effects of moderate exercise and oat β-glucan on innate immune function and susceptibility to respiratory infection" Am J Physiol Regul Integr Comp Physiol, Feb. 2004, pp. R366-R372, vol. 286.
Davis, J.Mark, et al., "Effect of Oat β-Glucan on Innate Immunity and Infection after Exercise Stress" Med. Sci. Sports Exerc., 2004, pp. 1321-1327, vol. 36, No. 8.
Everaerts, Frank et al., "Biomechanical properties of carbodiimide crosslinked collagen: Influence of the formation of ester crosslinks" Journal of Biomedical Materials Research Part A, May 2008, pp. 547-555, vol. 85, No. 2.
Goa KL, et al., "Hyaluronic acid. A review of its pharmacology and use as a surgical aid in ophthalmology, and its therapeutic potential in joint disease and wound healing" Drugs, Mar. 1994, pp. 536-566, vol. 47, No. 3.
Gu, Yeun-Hwa et al., "Enhancement of Radioprotection and Anti-Tumor Immunity by Yeast-Derived β-Glucan in Mice" Journal of Medicinal Food, 2005, pp. 154-158, vol. 8, No. 2.
Liu, Haifeng et al., "Construction of Chitosan-Gelatin-Hyaluronic Acid Artificial Skin in Vitro" Journal of Biomaterials Applications, Apr. 2007, pp. 413-430, vol. 21.
Mahmoud, Reyad et al., "Solubility and Hydrolyzability of Films Produced by Transglutaminase Catalytic Crosslinking of Whey Protein" Journal of Dairy Science, 1993, pp. 29-35, vol. 76.
Mattson, G. et al., "A practical approach to crosslinking" Molecular Biology Reports, 1993, pp. 167-183, vol. 17.
Nakayama, Grace R. et al., "Assessment of the Alamar Blue assay for cellular growth and viability in vitro" Journal of Immunological Methods, 1997, pp. 205-208, vol. 204.
Pongjanyakul, Thaned et al., "Xanthan-alginate composite gel beads: Molecular interaction and in vitro characterization" International Journal of Pharmaceutics, 2007, pp. 61-71, vol. 331.

(Continued)

*Primary Examiner* — Janet Epps-Smith
*Assistant Examiner* — Yanzhi Zhang
(74) *Attorney, Agent, or Firm* — Knobbe Martens Olson & Bear LLP

(57) ABSTRACT

The present invention relates to a composition comprising colostrum and at least one agent selected from the group of hydrocolloids, wherein said colostrum and at least one agent are bioconjugated. The bioconjugated composition has improved properties compared to colstrum compositions that are not bioconjugated with a hydrocolloid agent. The composition may be used in a variety of settings, for example for topical application for treating skin diseases and skin conditions. The present invention thus also relates to use of the composition and to a method for the preparation of the composition.

25 Claims, 20 Drawing Sheets

(56) References Cited

OTHER PUBLICATIONS

Schroecksnadel, Katharina et al., "Antioxidants Suppress Th1-Type Immune Response in Vitro" Drug Metabolism Letters, Aug. 2007, pp. 166-171, Abstract.

Thalmann, Claudia Rita et al., "Enzymatic cross-linking of proteins with tyrosinase" Eur Food Res Technol, 2002, pp. 276-281, vol. 214.

Widner, Bernhard et al., "Simultaneous Measurement of Serum Tryptophan and Kynurenine by HPLC" Clinical Chemistry, 1997, pp. 2424-2426, vol. 43.

Winkler, Christiana et al., "In Vitro Testing for Antiinflammatory Properties of Compounds" Clinical Chemistry, 2006, pp. 1201-1202, vol. 52, No. 6.

Wirleitner, B. et al., "Interferon-γ-Induced Conversion of Tryptophan: Immunologic and Neuropsychiatric Aspects" Current Medicinal Chemistry, 2003, pp. 1581-1591, vol. 10.

* cited by examiner

Figure 1
A.
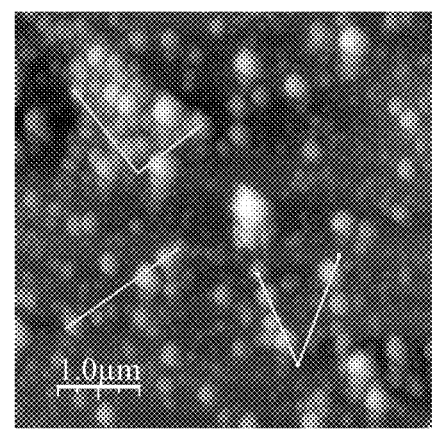 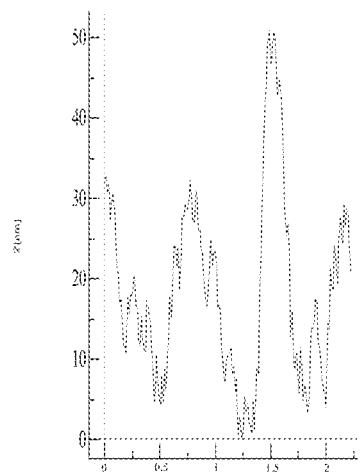
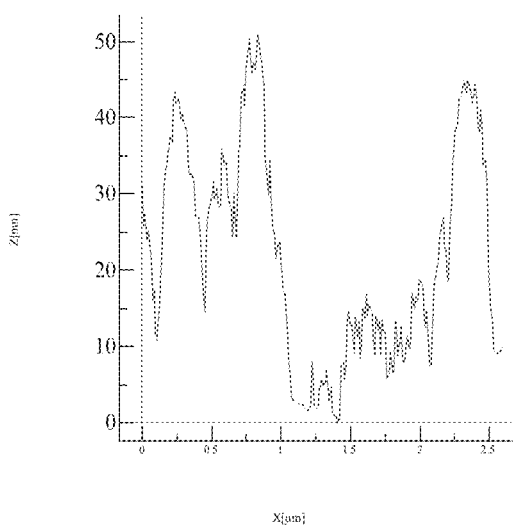 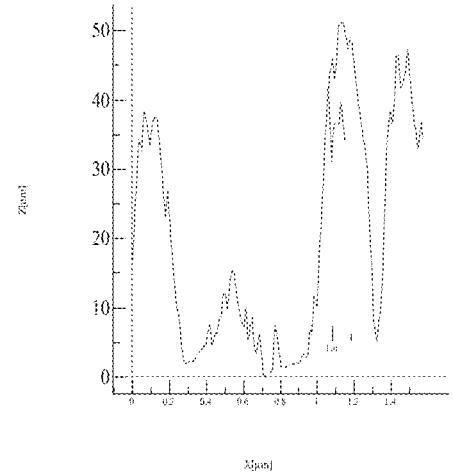

Figure 1 (Cont.)
B.
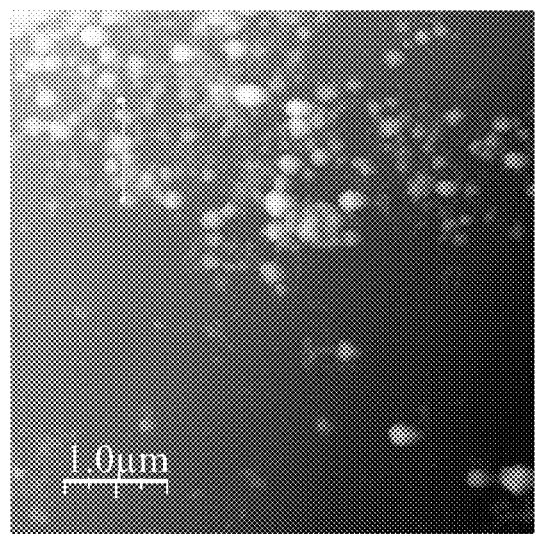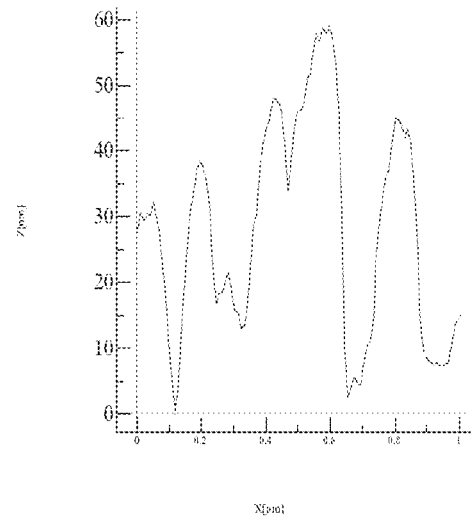

A.    B.

A.    B.

Figure 6
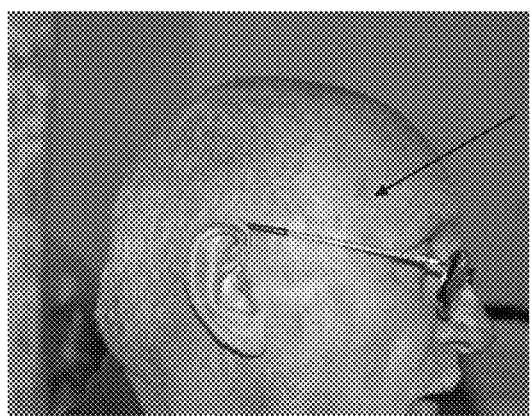
A.
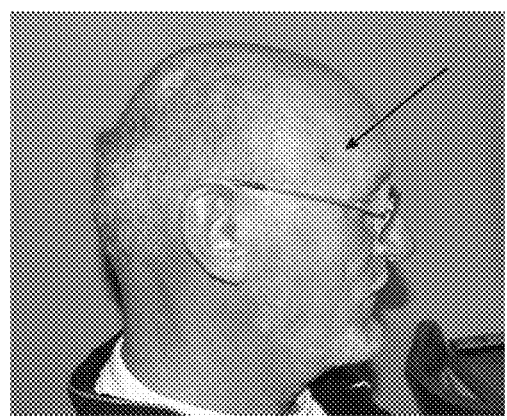
B.
Figure 7
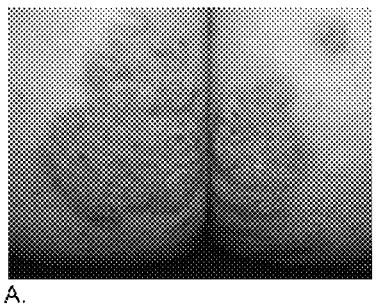
A.
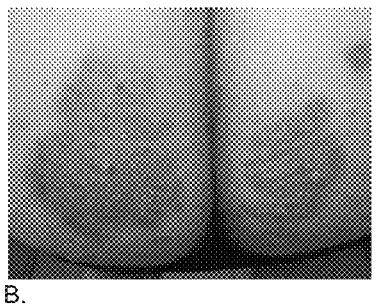
B.
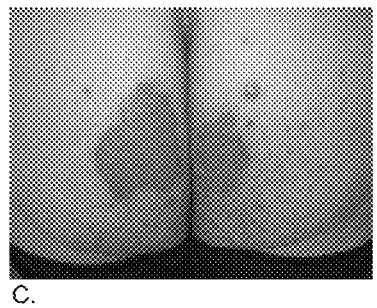
C.

Figure 8
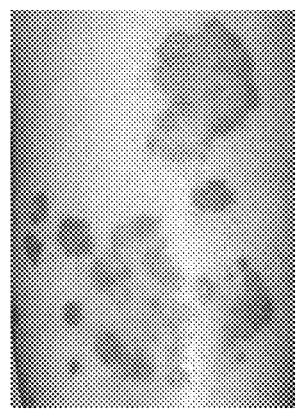
A.
B.
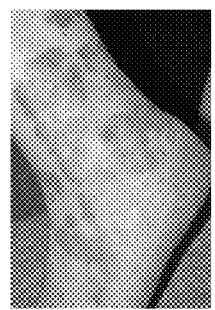
C.
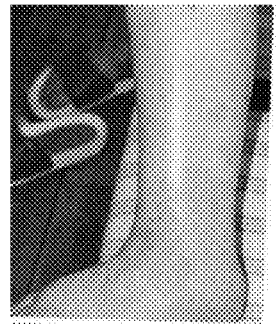
D.

Figure 9
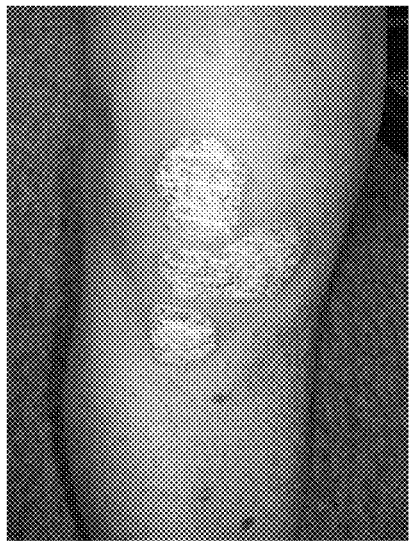
A.
B.
Figure 10
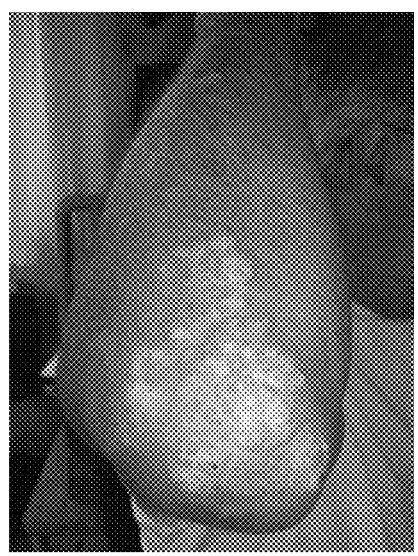
A.
B.

|  | Unstimulated | PHA [10 µg/ml] |
|---|---|---|
| Tryptophan [µmol/L] | 30.4 ± 1.9 | 8.2 ± 2.0 ** |
| Kynurenine [µmol/L] | 0.9 ± 0.1 | 9.8 ± 1.3 ** |
| Kyn/trp [µmol/mmol] | 28.1 ± 3.6 | 1312.3 ± 459.2 ** |
| Neopterin [µmol/L] | 3.6 ± 0.4 | 13.2 ± 3.6 ** |

COLOSTRUM COMPOSITION

CROSS REFERENCE TO RELATED APPLICATIONS

This application claims the benefit and priority to and is a U.S. National Phase Application of PCT International Application Number PCT/DK2009/050234, filed on Sep. 10, 2009, designating the United States of America and published in the English language, which is an International Application of and claims the benefit of priority to Danish Patent Application No. PA 2008 01286, filed on Sep. 12, 2008, and U.S. Provisional Application No. 61/105,507, filed on Oct. 15, 2008. The disclosures of the above-referenced applications are hereby expressly incorporated by reference in their entireties.

FIELD OF THE INVENTION

The present invention relates to a composition comprising colostrum and at least one agent selected from the group of hydrocolloids, wherein said colostrum and at least one agent are bioconjugated. The bioconjugated composition has improved resistance to proteolysis compared to compositions comprising bioconjugated colostrum. The composition may be used in a variety of settings, for example for topical application for treating skin conditions. The present invention thus relates to use of the composition and to a method for the preparation of the composition.

BACKGROUND OF INVENTION

Colostrum is a form of milk produced by mammals in late pregnancy and the few days after giving birth. Colostrum is also known as "immune milk" due to increased levels of components important in mediating immune responses, in particular immunoglobulins. In addition, colostrum is rich in protein, polysaccharides and important nutrients and vitamins. Thus, colostrum is regarded as a composition with beneficial healthcare properties. Most compositions containing colostrum are made by the addition of purified, freeze dried colostrum powder. (Wadstein, 2002, Rafkin, 2005). In human and animal cells, colostrum proteins have shown to interact through cell surface receptors and influence processes such as morphogenesis, wound repair and anti-inflammatory processes. But these factors can be limited due to the poor mechanical properties, rapid degradation and in vivo clearance when powdered colostrum is used.

The food industry is constantly on the lookout for new and better food-ingredients for potential enhancement of the rheological properties of processed food.

It is in the consumer's interest to minimize the use of additives. Therefore it is of interest to be able to modify the functionality of original food components, whereby the use of additives with declaration obligations can be minimised. Modifications of milk proteins to improve their gelling properties may involve agglomeration, or alterations of the surface of milk proteins to enhance the water-binding properties of the proteins. The aim of the process for agglomeration of dairy proteins in industry is to improve the functionality of available milk proteins producing more viscosity and enhancing texture.

In yogurt, the agglomeration of whole milk proteins increases viscosity and decreases syneresis by improving the water holding capacity of the gel. This can lead to standard formulations with a richer, high-quality texture or reformulated products that maintain the expected creamy mouth feel.

Hyaluronic acid and (salts thereof) is a type of hydrocolloid and is a non-sulphated member of the family of glycosaminoglycans, a diverse group of compounds involved in critical functions within the eukaryote cell. Hyaluronic acid is well known for its large water binding capacity, and hence moisturising properties.

Compositions containing a mixture of colostrum, or parts of colostrum, and hyaluroniuc acid are well known in a number of applications, including inhibition of bacterial growth (US20070110758), oxidative stress regulation (U.S. Pat. No. 6,939,847), nutritional supplements (WO2007/112716 and WO2007/112717) and cosmetic and/or pharmaceutical compositions (WO2007/009790, WO2007/039124, WO2007/000651).

SUMMARY OF INVENTION

The present invention relates to a composition comprising colostrum and at least one agent selected from the group of hydrocolloids, wherein said colostrum and at least one agent are bioconjugated. Thus, in a first aspect the invention relates to a composition comprising colostrum or part thereof and at least one agent selected from hydrocolloids, wherein said colostrum and/or said colostrum and said at least one agent are bioconjugated.

The composition can be used as a pharmaceutical for the treatment of a number of diseases. Therefore, in a second aspect, the present invention relates to a pharmaceutical composition comprising the composition as described above.

The present invention also in a third aspect relates to a method for producing the composition as described above. Consequently, a fourth aspect pertains to a method for the preparation of the composition as described herein comprising the steps of a) providing colostrum or part thereof, providing at least one agent, c) mixing said colostrum or part thereof and said at least one agent, d) providing at least one cross-linking agent, e) mixing said colostrum or part thereof, said at least one agent and said at least one cross-linking agent, e) obtaining a bioconjugate.

It is within the scope of the present invention that the composition as described herein may be obtainable by the method described for the preparation of the composition. Thus, another aspect relates to a composition obtainable by the method described herein.

The present invention in further aspects relates to the use of the composition for the manufacture of a medicament, use of the composition as a medicament, use of the composition as an agent for topical application, use of the composition for skin conditions, use of the composition as a cosmetic agent, as an anti-wrinkle agent, use of the composition as a moisturising agent.

In a final aspect the present invention relates to a method of treatment of skin conditions comprising administration of the composition of the present invention in a therapeutically effective amount to an animal in need thereof.

DESCRIPTION OF DRAWINGS

FIG. 1. A. Atomic force microscopy (AFM) pictures of the colostrum bioconjugates according to the present invention. Low lactose colostrum bioconjugates. B. Bioconjugates with low lactose colostrum and high molecular weight hyaluronic acid. Size of particles between 30-60 nm. Observations were made on a Light Lever AFM Scanner (Model no. P-01-0005-0) from Pacific Nanotechnology.

Within 20 hours, 80% of the bioconjugates not containing hyaluronic acid are destroyed and the proteolysis products are detected in the supernatant as measured by the BioRad protein assay. But the bioconjugates containing hyaluronic acid is resistant to proteolysis after 20 hours incubation with acid protease. However at 48 hours 60% of the hyaluronic acid containing colostrum bioconjugates is destroyed as compared to the 80% destruction of bioconjugates only containing colostrum. Thus using a long chain carbohydrate polymer to make the colostrum aggregates helps in protection against protease activity and can be incorporated in slow release bioconjugate formulations of active ingredients.

Figure 3:
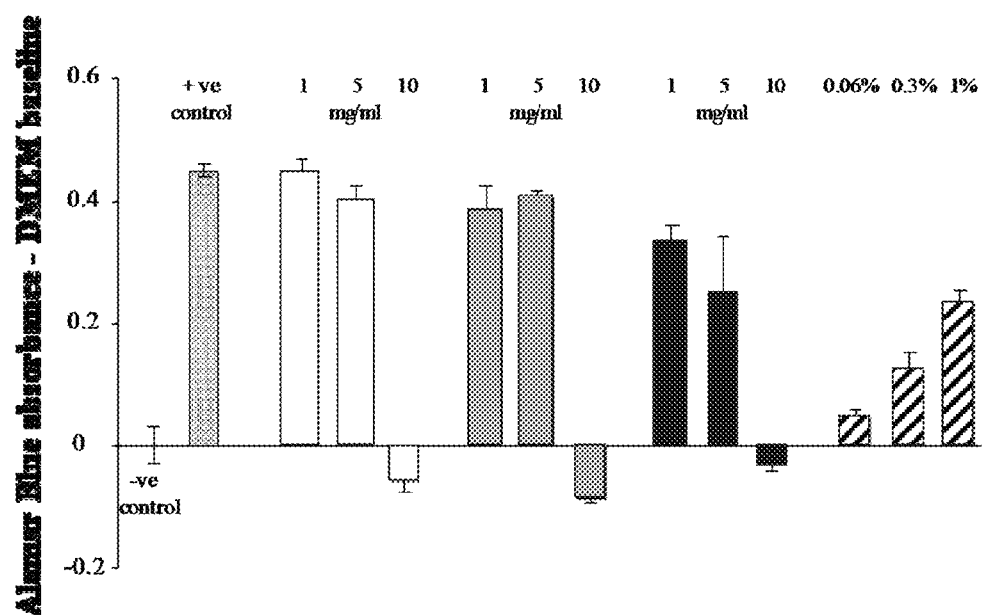

FIG. 3. Cell proliferation assay using the colostrum bioconjugate in a basis cream. Proliferation studies using an epithelial cell line (HT29) were conducted with 3 preparations (Sample 1+Euxyl, Sample 2+Euxyl and Sample 3+Euxyl) of bioconjugated colostrum for their ability to enhance cell proliferation in case of wounding. As it can be seen that all 3 samples are able to promote cell proliferation and healing, processes essential in case of cell injury.

Figure 4:
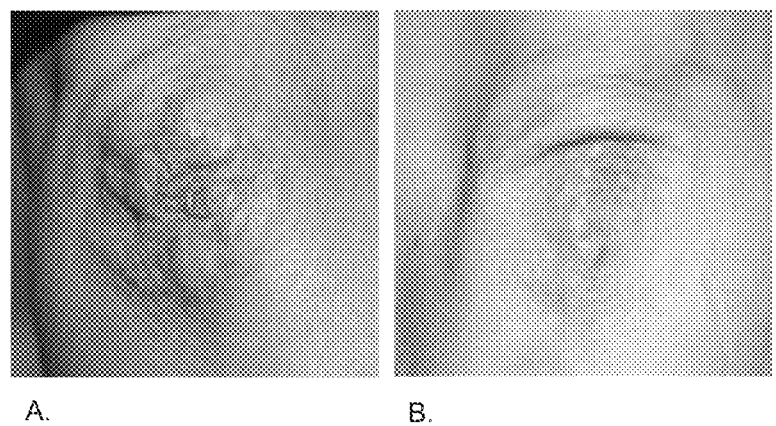

FIG. 4. A. Before use of the colostrum bioconjugate. B. After 7 days of use of the colostrum bioconjugate. The colostrum bioconjugate in a basis cream used for 7 days on a patient with skin eruption with itch on the elbow due to intake of excess pain killing medicine. The patient has been suffering for 20 years and has tried several cosmetic creams without effect. The patient has used the skin cream with colostrum composition of the present invention and the itch and the eruption has receded after 2 days and disappeared after 7 days.

Figure 5:
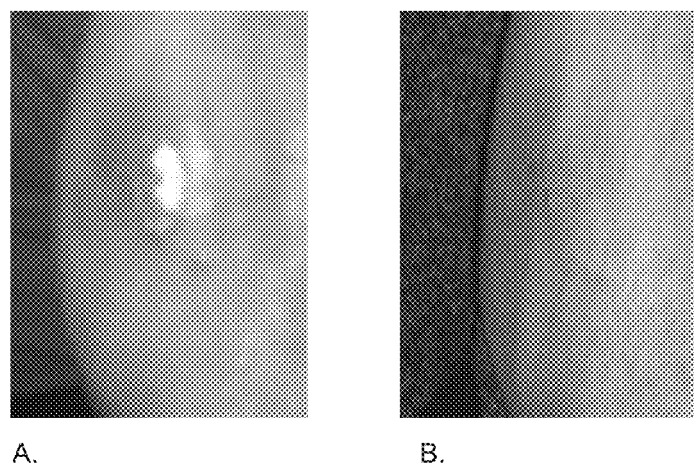

FIG. 5. A. Before use of the colostrum bioconjugate. B. After 8 days of use of the colostrum bioconjugate. The colostrum bioconjugate of the present invention in a basis cream used on difficult to heal post-operative wound. Before use of the cream of the present invention, the wound would not heal for several months. The patient applied the composition of the present invention on the wound at mornings and evenings for 8 days.

FIG. 6. A. Before use of the colostrum bioconjugate, the patient was treated for skin cancer 5 years ago with probable relapse. Arrow indicates site of constant bleeding for almost a year showing signs of probable relapse. B. 2 weeks after use of the colostrum bioconjugate, the wounds have healed and the patient's wound has ceased bleeding. Arrow indicates site of healing of sores. The patient applied the colostrum bioconjugate of the present invention.

FIG. 7. Cream used on psoriasis patient suffering from severe psoriasis for 16 years. A. Before use of the colostrum bioconjugate. B. 2 weeks of using the colostrum bioconjugate. C. 45 days after using skin cream with the bioconjugated colostrum composition of the present invention.

FIG. 8. Cream used on psoriasis patient suffering for more than 33 years. A and C. 2 months of using a colostrum composition without hydrocolloids. The itching, scaling and inflammation of the skin disappeared but the red plaques/discoloration did not disappear. B and D. After 2 more months of using the composition of the present invention comprising bioconjugated colostrum and hydrocolloids, the plaques disappeared.

FIG. 9. Cream used on patient suffering from psoriasis on the knee for about 15 years. A. Before use of cream. B. 2 weeks of using the skin cream comprising the colostrum bioconjugate of the present invention there is disappearance of scaliness and overproduction of skin cells.

FIG. 10. Cream used on patient with psoriasis on the elbow for 20 years. A. Before use of cream. B. 2 weeks of using the skin cream comprising the colostrum bioconjugate of the present invention there is disappearance of scaliness and overproduction of skin cells.

Figure 11:
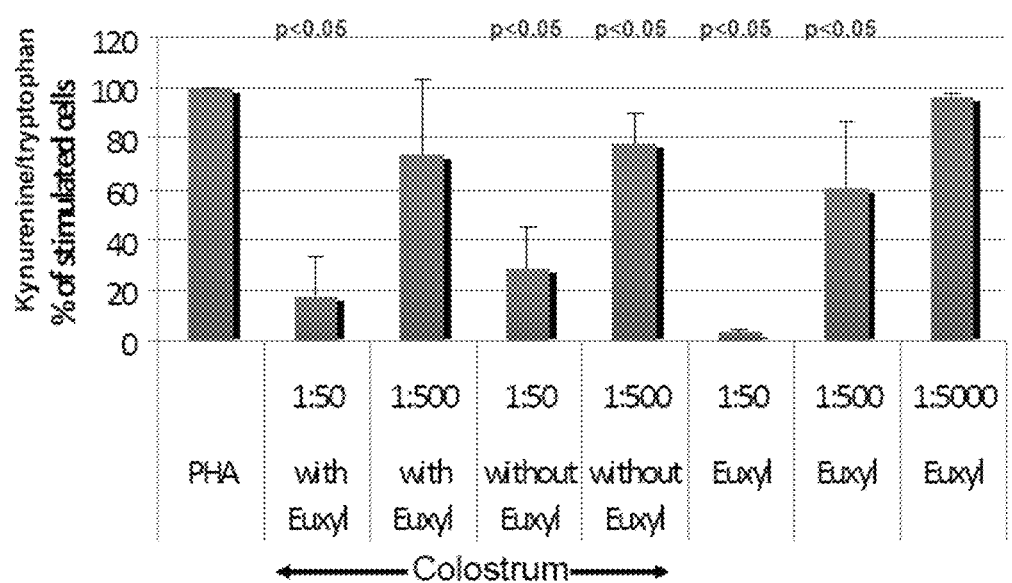

FIG. 11. Tryptophan degradation in PHA-stimulated cells. 10 μg PHA/ml was used for stimulation of the PBMCs. PBMCs incubated with colostrum with/without Euxyl and with pure Euxyl. Pure colostrum preparation suppresses mitogen-induced tryptophan degradation in a dose-dependent way. Euxyl has a stronger effect and when euxyl is added to colostrum the suppressive effect also becomes stronger. The effect of euxyl is similar to other preservatives (Schroecksnadel et al., 2007).

Figure 12:
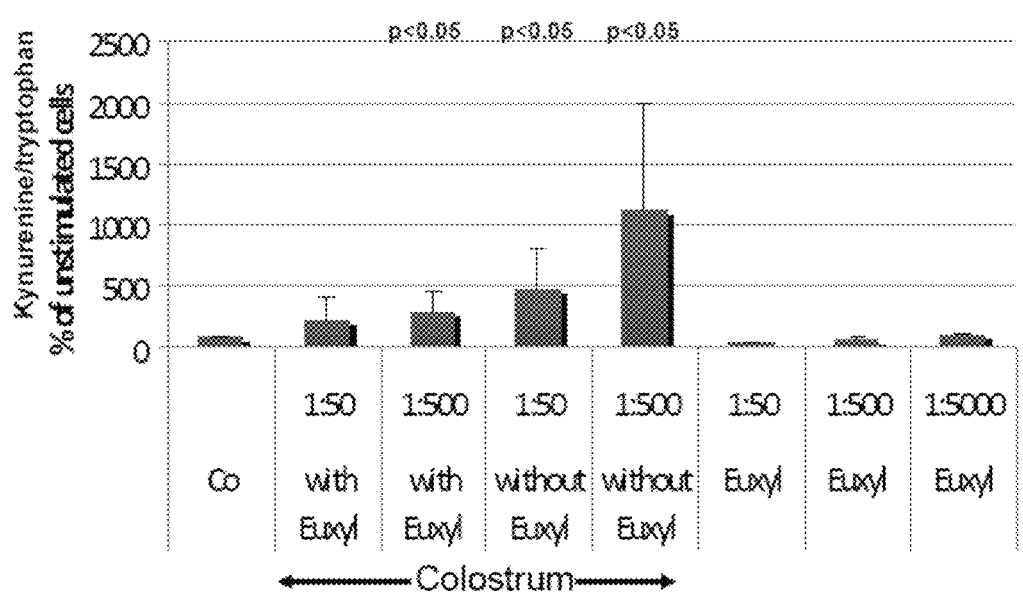

FIG. 12. Tryptophan degradation on unstimulated PBMCs incubated with colostrum with/without Euxyl and with pure Euxyl. As control, cells were treated with medium alone. It can be seen that colostrum has a stimulatory effect on tryptophan degradation, whereas euxyl has an inhibitory effect. Surprisingly, it can be seen that the higher dilution of colostrum seems to have a stronger effect especially on tryptophan degradation.

Figure 13:
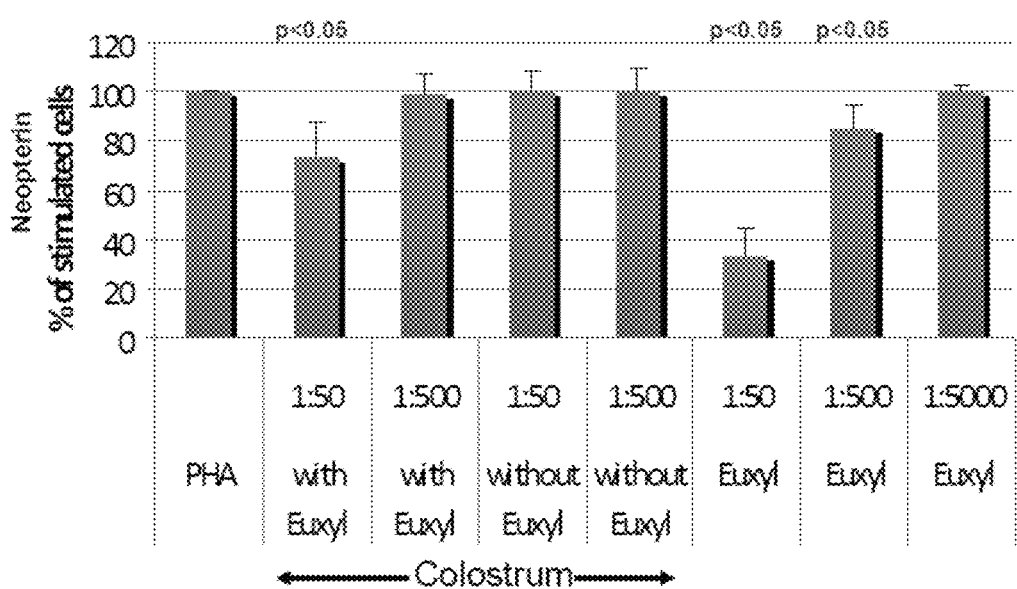

FIG. 13. Neopterin production in on PHA-stimulated cells were incubated with colostrum with/without Euxyl and with pure Euxyl. 10 μg PHA/ml was used for stimulation of the PBMCs. Pure colostrum does not suppress PHA-stimulated PBMCs in a dose dependent fashion. Colostrum has a stimulatory effect on neopterin production. Euxyl has a stronger effect and when euxyl is added to colostrum the suppressive effect also becomes stronger and is also active to suppress neopterin production.

Figure 14:
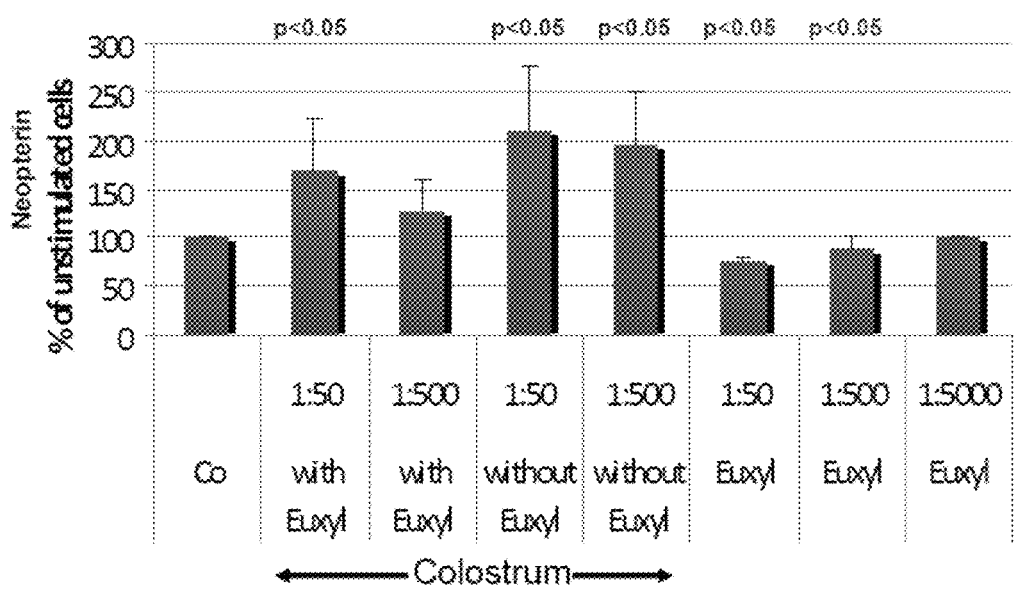

FIG. 14. Neopterin production in unstimulated cells. Cells were incubated with colostrum with/without Euxyl and with pure Euxyl. As control, cells were treated with medium alone Colostrum has a stimulatory effect on neopterin production whereas euxyl still has an inhibitory effect.

Figure 15:
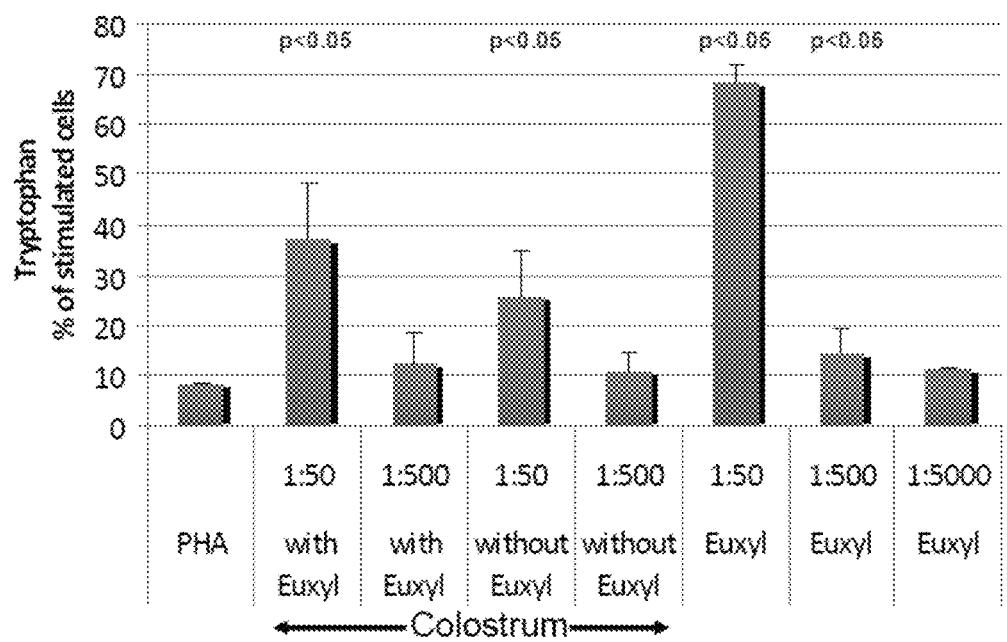

FIG. 15. Decline of tryptophan in PHA-stimulated PBMCs treated with colostrum with/without Euxyl and with pure Euxyl. 10 □g PHA/ml was used for stimulation of the PBMCs. The colostrum preparation suppresses mitogen-induced tryptophan degradation in a dose-dependent way. Euxyl has a stronger effect and when euxyl is added to colostrum the suppressive effect also becomes stronger.

Figure 16:
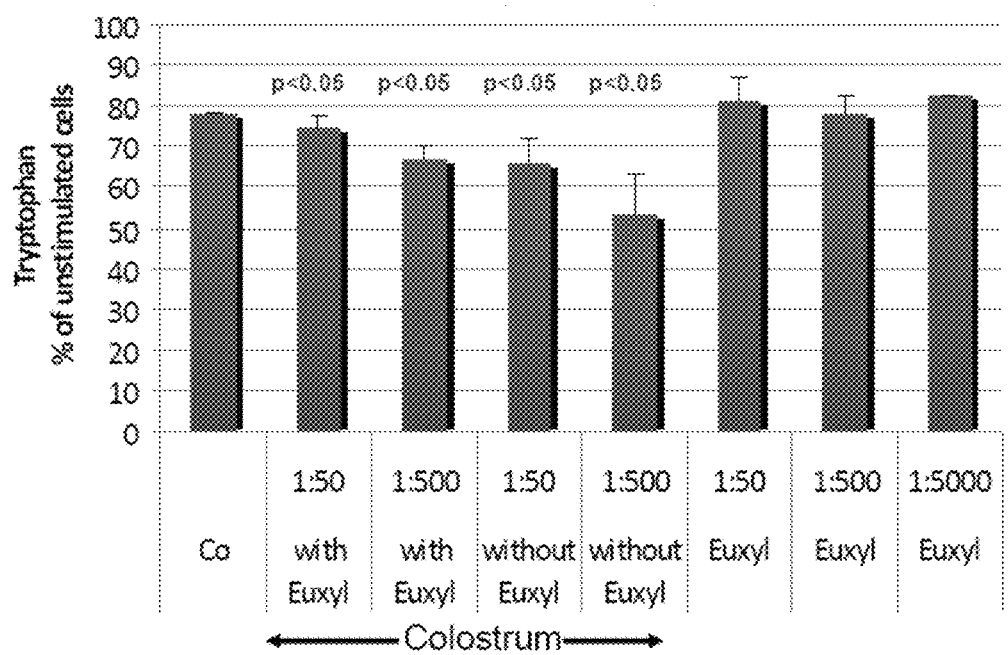

FIG. 16. Decline of tryptophan in unstimulated PBMCs treated with colostrum with/without Euxyl and with pure Euxyl. As control, cells were treated with medium alone. Colostrum has a stimulatory effect on tryptophan degradation whereas euxyl has an inhibitory effect. Surprisingly, higher dilution of colostrum seems to have a stronger effect on tryptophan degradation in unstimulated cells.

Figure 17:
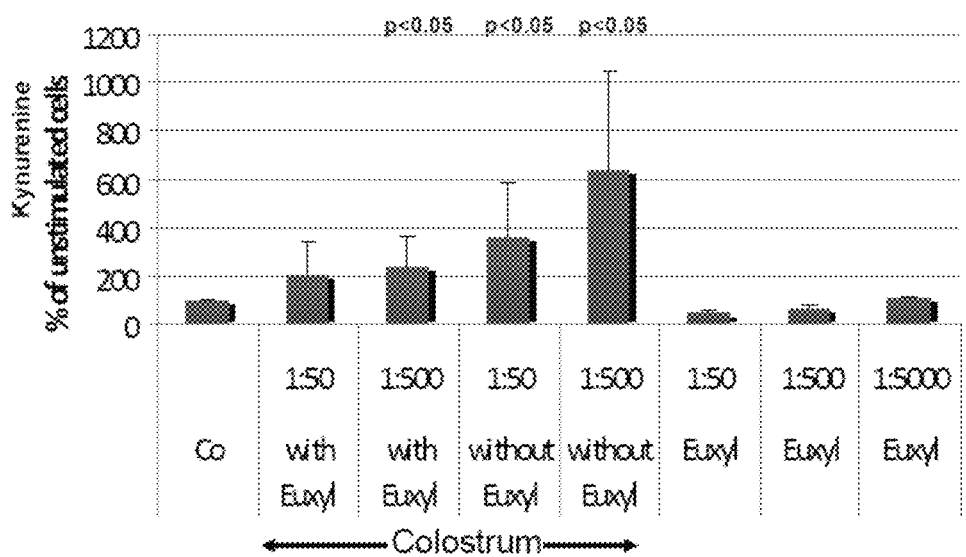

FIG. 17. Kynurinine production in unstimulated PBMCs treated with colostrum with/without Euxyl and with pure Euxyl. As control, cells were treated with medium alone. In unstimulated PBMCs, colostrum with and without the presence of euxyl is instrumental in decreasing knyurinine production in a dose dependent fashion. Pure Euxyl has no effect.

Figures 18, 19:
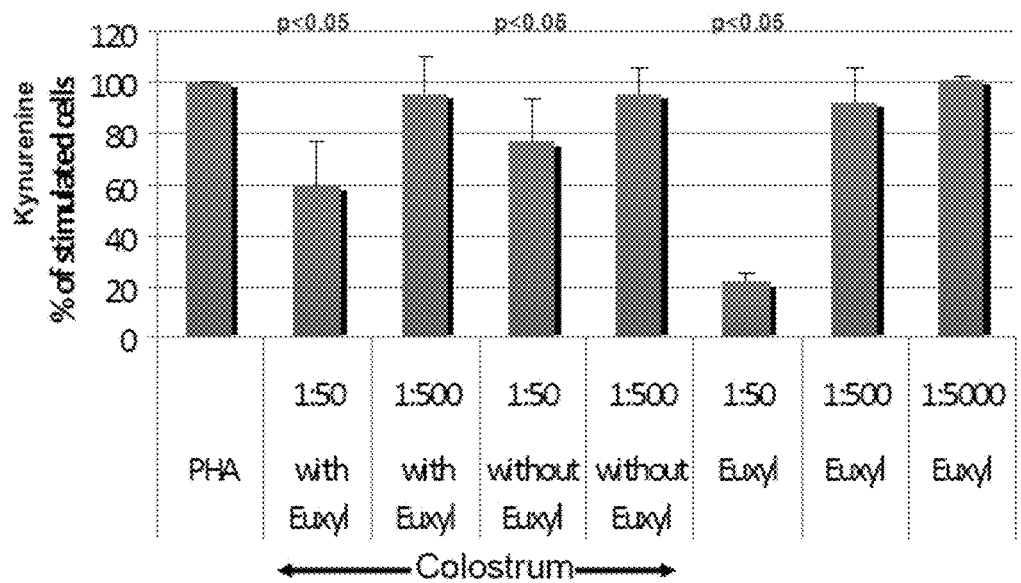

FIG. 18. Kynurinine production in PHA-stimulated PBMCs treated with colostrum with/without Euxyl and with pure Euxyl 10 μg PHA/ml was used for stimulation of the PBMCs. As control, cells were treated with medium alone. There is a decrease in knyurenine production in a dose dependent fashion when colostrum with/without euxyl is added to stimulated PBMCs.

FIG. 19: Concentrations of tryptophan, kynurenine, kynurenine to tryptophan ratio (kyn/trp) and neopterin in the supernatant of unstimulated PBMC and in cells stimulated with 10 μg/ml phytohaemagglutinin (PHA) for 48 h. Results shown are the mean values±S.E.M. of three independent experiments run in duplicates (**p<0.005, compared to unstimulated cells).

Figure 20:
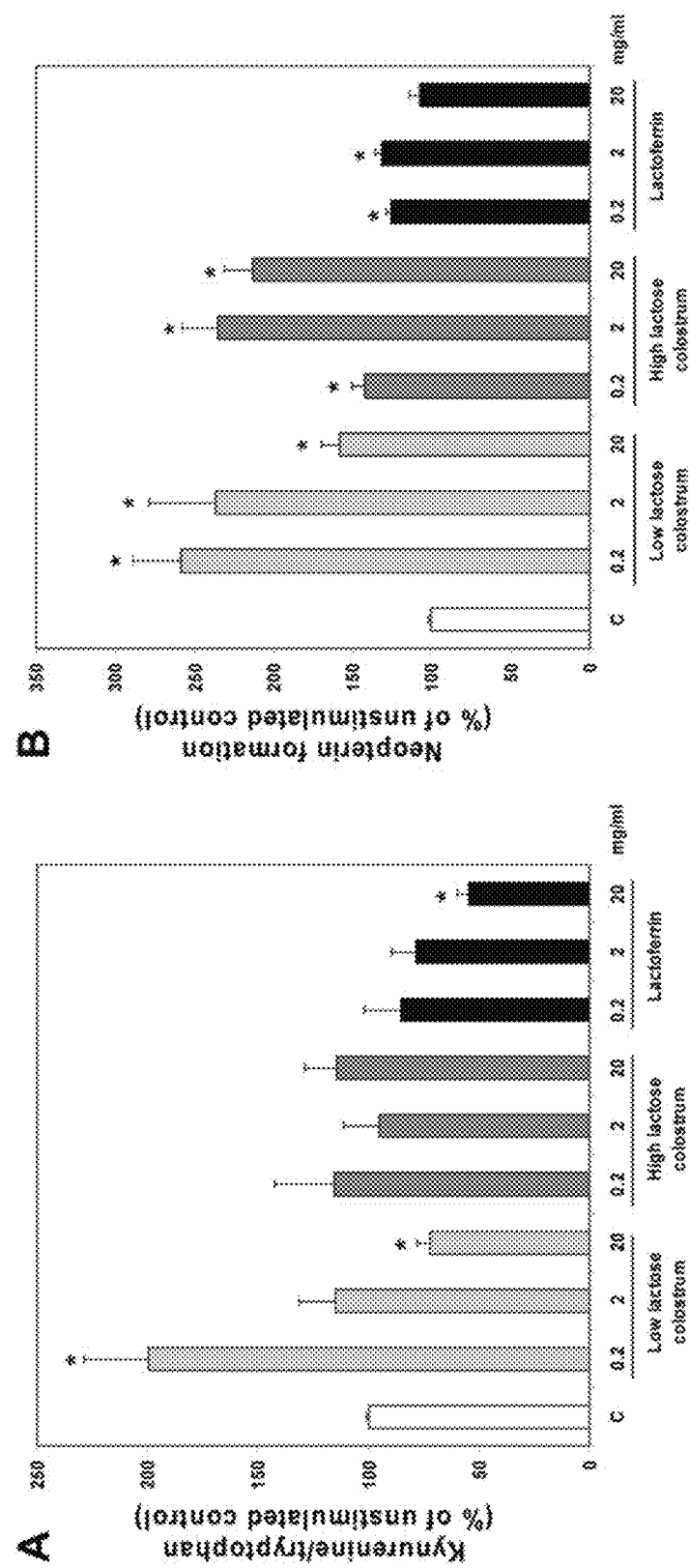

FIG. 20: A. Kynurenine to tryptophan ratio and *B. neopterin* formation expressed as % of unstimulated control (C) in PBMC treated or not with increasing concentrations of bovine colostrum with low and higher amounts of lactose and lactoferrin alone for 48 h. Results shown are the mean values±S.E.M. of three independent experiments run in duplicates (*p<0.05).

Figure 21:
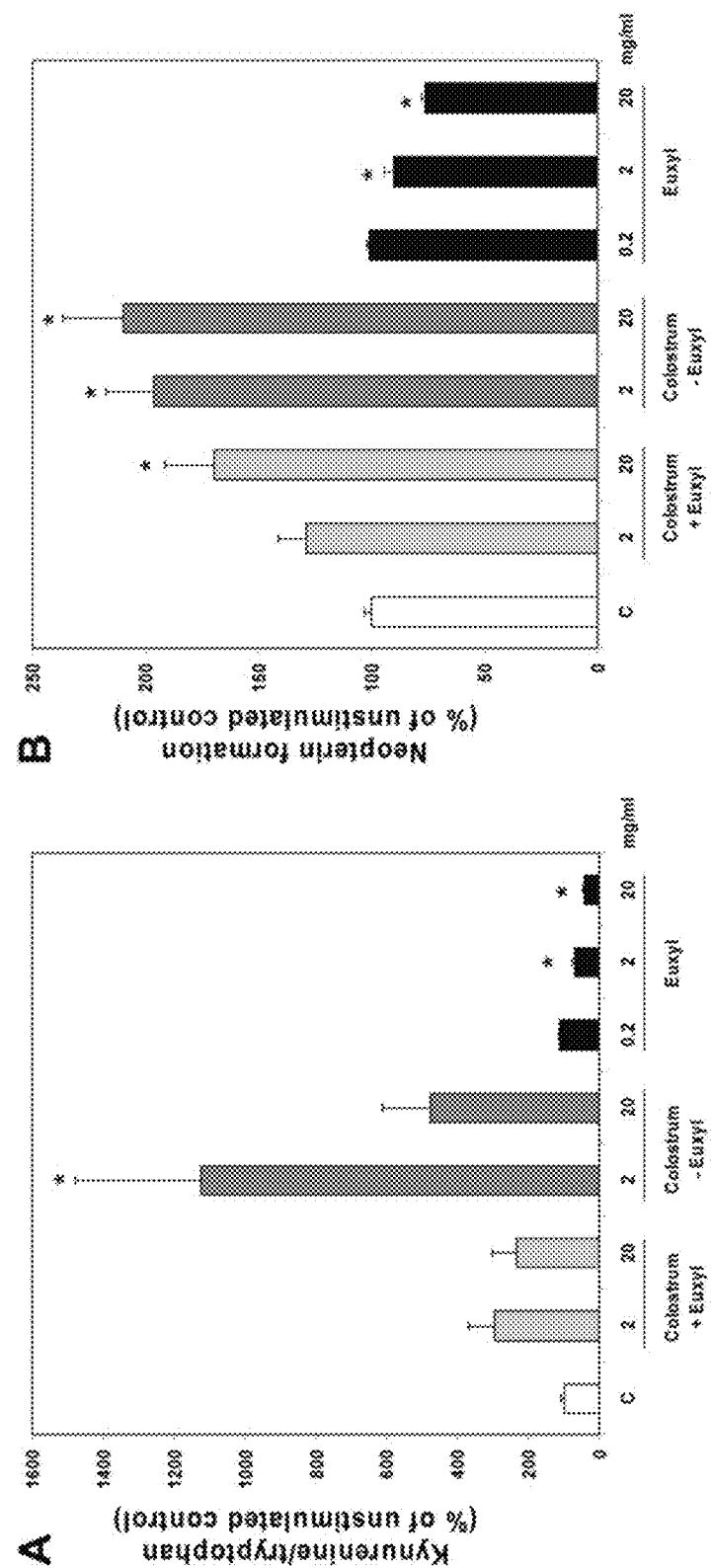

FIG. 21: A. Kynurenine to tryptophan ratio and *B. neopterin* formation expressed as % of unstimulated control (C) in PBMC treated or not with increasing concentrations of bovine colostrum with or without euxyl and euxyl alone for 48 h. Results shown are the mean values±S.E.M. of three independent experiments run in duplicates (*p<0.05).

Figure 22:
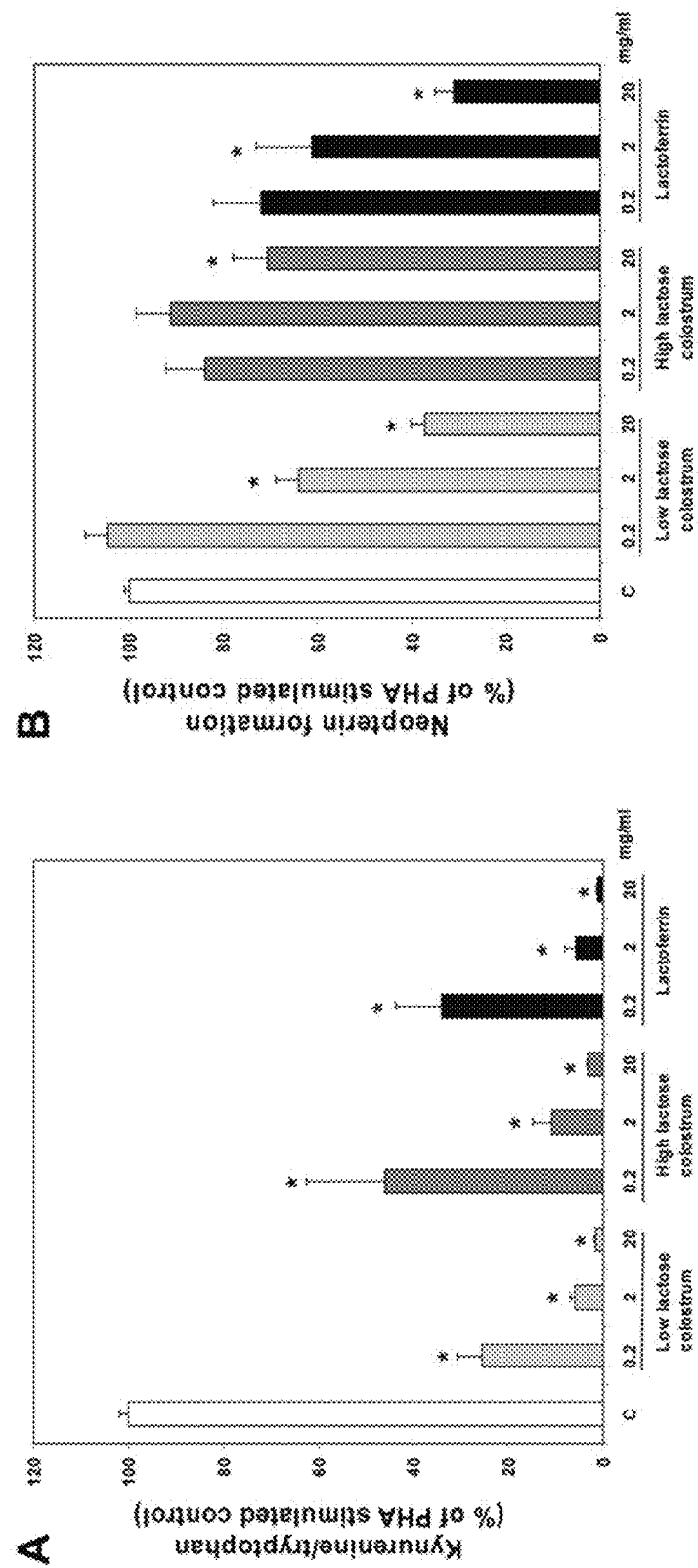

FIG. 22: A. Kynurenine to tryptophan ratio and *B. neopterin* formation expressed as % of phytohaemagglutinin (PHA, 10 µg/ml) control (C) in PBMC cotreated or not with increasing concentrations of bovine colostrum with low and higher amounts of lactose and lactoferrin alone for 48 h. Results shown are the mean values±S.E.M. of three independent experiments run in duplicates (*p<0.05).

Figure 23:
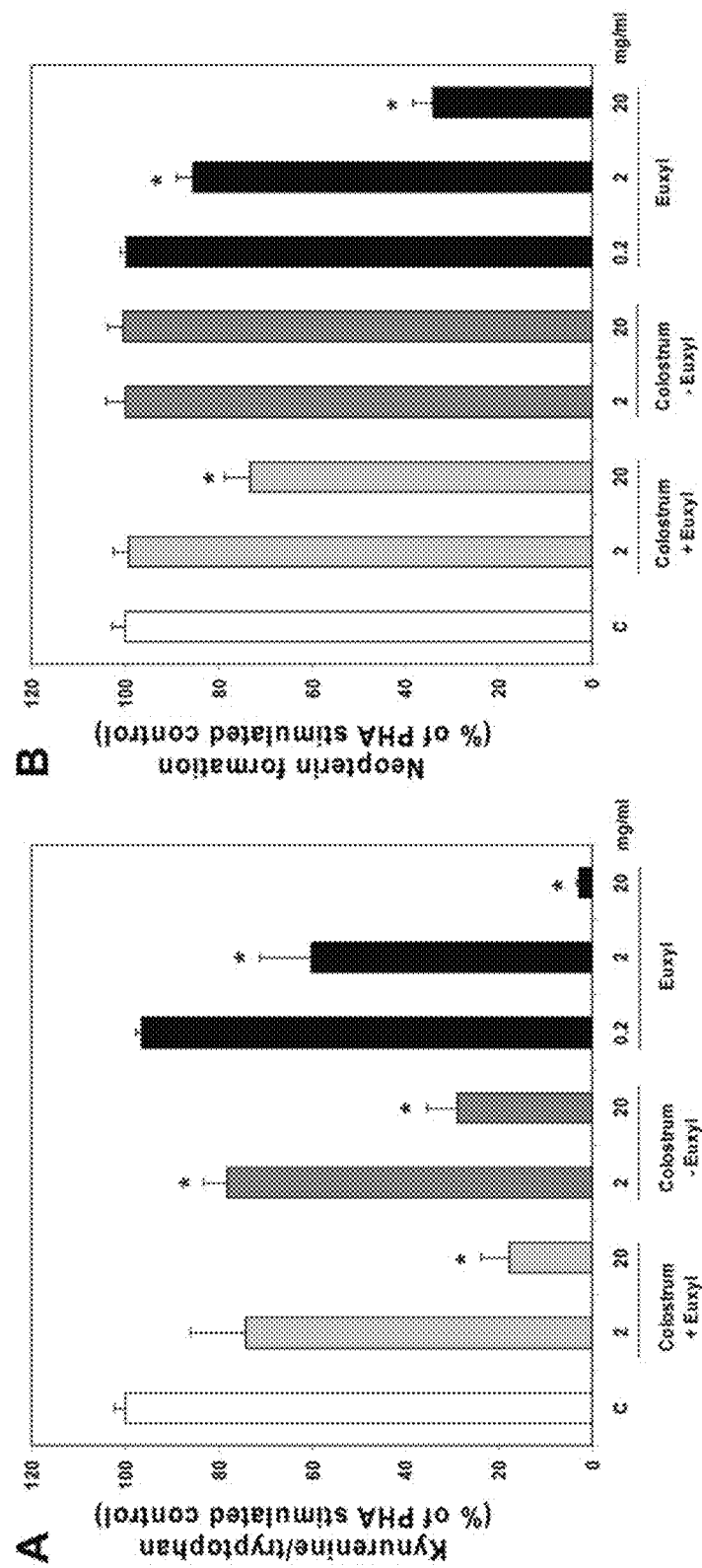

FIG. 23: A. Kynurenine to tryptophan ratio and *B. neopterin* formation expressed as % of phytohaemagglutinin (PHA, 10 µg/ml) control (C) in PBMC cotreated or not with increasing concentrations of bovine colostrum with or without euxyl and euxyl alone for 48 h. Results shown are the mean values±S.E.M. of three independent experiments run in duplicates (*p<0.05).

DETAILED DESCRIPTION OF THE INVENTION

The present invention relates to a composition comprising colostrum or part thereof and at least one agent selected from hydrocolloids, wherein said colostrum and/or said colostrum and said at least one agent are bioconjugated.

The present invention makes use of colostrum and hydrocolloids, e.g. hyaluronic acid, combined with cross-linking agents resulting in a novel composition comprising bioconjugated particles. The size of these bioconjugates facilitates penetration of the active components into the skin and direct cellular processes within the skin. In addition, the bioconjugated composition has increased immunostimulatory and anti-inflammatory effects, compared to similar compositions not comprising bioconjugates. Furthermore, the composition comprising bioconjugated particles has superior properties regarding degradation and in vivo clearance, compared to similar compositions not comprising bioconjugates.

The presence of hydrocolloids together with the various components of colostrum during bioconjugation increases the synergy between the components of colostrum compared to bioconjugation of the individual components in the absence of hydrocolloids.

The bioconjugation of said colostrum or part thereof and at least one agent selected from hydrocolloids provides the composition with improved resistance to for example proteolysis and thus improving the applicability of the composition.

Incorporation of hyaluronic acid or xanthan gum or sodium alginate or beta-glucan together with the agglomerated (bioconjugated) proteins may probably increase the biomedical application of the skin cream.

Colostrum

Colostrum is a form of milk produced by mammals in late pregnancy and the few days after giving birth. Colostrum is high in carbohydrates, in particular lactose, protein, and antibodies (immunoglobins). Colostrum contains all five immunoglobulins found in all mammals, (A, D, G, E and M) and the total amount of immunoglobins may be up to 10% of the total protein content in colostrum. Other proteins in colostrum include lactoferrin, lactalbumin, lactoglobin, lactoperoxidase and growth factors, in particular IGFs, and peptides such as PRPs (praline rich polypeptides). In addition, colostrum contains fat, vitamins, and nutrients.

In one embodiment of the present invention, the colostrum or part thereof, originates from bovine, equine, porcine, human, ovine, caprine or cervidae. However, in another embodiment the colostrum or part thereof is of bovine, porcine or human origin. In a preferred embodiment the colostrum is of bovine origin.

According to the present invention, the composition comprises whole colostrum or part thereof. The main components of colostrum are fat, protein, lactose, minerals, immunoglobulins (IgA, IgD, IgG, IgE and IgM), lactoferrin, water and fat soluble vitamins, respectively. An example of the distribution of the main components of bovine colostrum is given below:
Example of the Distribution of the Main Components of Bovine Colostrum

| | |
|---|---|
| Fat | 6.7% w/w |
| Protein | 14.9% w/w |
| Lactose | 2.5% w/w |
| Ash (minerals) | 0.05% w/w |
| Immunoglobins | 47.5 mg/ml |
| Lactoferrin | 0.8 mg/ml |
| Vitamins (fat soluble) | 8.0 µg/ml |
| Vitamins (water soluble) | 6.8 µg/ml |

In one embodiment of the present invention, the compositions contain whole colostrum. In another embodiment, the compositions of the present invention comprise for example parts of whole colostrum. In one embodiment fats and/or lactose is removed from the colostrum. In another embodiment the composition comprises immunoglobulins and lactoferrin of colostrum. For example the composition comprises at least IgA, IgM and lactoferrin of colostrum. In yet another embodiment the composition of the present invention comprises at least least IgA, IgM, IgG and lactoferrin of colostrum. In yet another embodiment the composition of the present invention comprises at least IgA, IgM, IgG, lactoferrin and beta-lactoglobulin of colostrum. In a further embodiment the composition of the present invention comprises at least IgA, IgM, IgG, lactoferrin, beta-lactoglobulin and alpha-lactalbumin of colostrum.

In a preferred embodiment the composition of the present invention comprises at least IgA, IgM, IgG, lactoferrin, beta-lactoglobulin, alpha-lactalbumin and IGF-1 of colostrum.

In one embodiment the composition of the present invention comprises the following components in the following amounts of total bioconjugated proteins of colostrum: Lactoferrin in a concentration between 1-100 µg/ml, beta-lactoglobulin in a concentration between 1000-4000 ng/ml, alpha-lactalbumin in a concentration between 1000-4000 ng/ml, IgG in a concentration between 1-10 mg/ml, IgA in a concentration between 0.05-3.00 mg/ml, IgM in a concentration between 0.05-4.00 mg/ml and IGF-1 in a concentration between 1-15 ng/ml.

In another embodiment the composition of the present invention comprises the following components in the following amounts of total bioconjugated proteins of colostrum: Lactoferrin in a concentration between 10-50 µg/ml, beta-lactoglobulin in a concentration between 2000-3000 ng/ml, alpha-lactalbumin in a concentration between 2000-3000 ng/ml, IgG in a concentration between 3-8 mg/ml, IgA in a concentration between 0.08-2.00 mg/ml, IgM in a concentration between 1-3 mg/ml and IGF-1 in a concentration between 2-10 ng/ml.

In a preferred embodiment the composition of the present invention comprises the following components in the following amounts of total bioconjugated proteins of colostrum: Lactoferrin in a concentration of at least 35 µg/ml, beta-lactoglobulin in a concentration of at least 2300 ng/ml, alpha-lactalbumin in a concentration of at least 2200 ng/ml, IgG in a concentration of at least 4 mg/ml, IgA in a concentration of at least 0.15 mg/ml, IgM in a concentration of at least 1 mg/ml and IGF-1 in a concentration of at least 5 ng/ml.

Colostrum may be collected from the birth-giving animal a few days before to some days after delivery of the offspring. In one embodiment of the present invention the colostrum used for the preparation of the composition is colostrum or part thereof collected up to 72 hours after delivery of the offspring. However, in a preferred embodiment of the present invention, the colostrum or part thereof is collected up to 48 hours of delivery.

It is also beneficial to agglomerate the entire proteins from colostrum rather than just a few proteins, as the combination of the proteins is necessary for the healing processes in the skin as has been seen with our results. Agglomerated colostrum proteins made from milking after 6 hours containing a maximum of antibodies was not able to exert the same healing effect as was in the case with agglomerated protein made from collecting colostrums after 48 hours.

According to the present invention the composition comprises 1% to 95% (w/w) colostrum of the total composition, such as 5% to 95%, for example 10% to 95%, such as 15% to 95%, for example 20% to 90%, such as 25% to 95%, 30% to 95%, 35% to 95%, for example 40% to 95%, such as 45% to 95%, 50% to 95%, 55% to 95%, 60% to 95%, for example 65% to 95%, such as 70% to 95%, 75% to 95%, 80 to 95%, 85% to 95%, for example 90% to 95%.

In another embodiment the composition of the present invention comprises 1% to 75% (w/w) colostrum of the total composition, such as 5% to 75%, for example 10% to 75%, such as 15% to 75%, for example 20% to 75%, such as 25% to 75%, 30% to 75%, 35% to 75%, for example 40% to 75%, such as 45% to 75%, 50% to 75%, 55% to 75%, 60% to 75%, for example 65% to 75%, such as 70% to 75%.

In yet another embodiment the composition of the present invention comprises 1% to 50% (w/w) colostrum of the total composition, such as 5% to 50%, for example 10% to 50%, such as 15% to 50%, for example 20% to 50%, such as 25% to 50%, 30% to 50%, 35% to 50%, for example 40% to 50%, such as 45% to 50%.

In a further embodiment the composition of the present invention comprises 1% to 35% (w/w) colostrum of the total composition, such as 5% to 35%, for example 10% to 35%, such as 15% to 35%, for example 20% to 35%, such as 25% to 35%, 30% to 35%.

In an even further embodiment, the composition of the present invention comprises colostrum which was originally fresh liquid, fresh-frozen, frozen or freeze-dried.

In a preferred embodiment the composition of the present invention comprises colostrum in the range of 1% to 30% (w/w) of the total composition, such as 5% to 30%, 10% to 30%, for example 15% to 30%, 20% to 30%, such as 25% to 30%. In a further preferred embodiment the composition of the present invention comprises colostrum in the range of 5% to 25% (w/w) of the total composition, such as 10% to 25%, for example 15% to 25%, such as 20% to 25%. In yet a preferred embodiment the composition of the present invention comprises colostrum in the range of 1% to 20% (w/w) of the total composition, such as 5% to 20%, for example 10% to 20%, 15% to 20%, or 5% to 15%, such as 10 to 15%.

In an especially preferred embodiment, the colostrum of the present invention is whole colostrum without fat and/or lactose of bovine origin, collected up to 48 hours of delivery, which was originally freeze-dried and wherein the amount of colostrum is in the range 5% to 30% (w/w) of the total composition.

Agents

In addition to colostrum, the present invention comprises at least one agent selected from hydrocolloids.

In one embodiment of the present invention the hydrocolloid is selected from the group consisting of agar/agar, starch and its derivatives, potato starch, carrageenan, guar gum, pectin and its derivatives, xanthan gum, alginate, arabinoxylan, cellulose and its derivatives, carboxymethyl cellulose, chitin, xylan, curdlan, beta-glucan, gum Arabic, locust bean gum, hyaluronic acid, gelatine and soya protein. It is within the scope of the present invention that the hydrocolloid may be selected individually from the group in separate embodiments.

Agar or agar/agar is a gelatinous substance derived from seaweed. Starch is a branched glucose polymer with beta-1, 4/1,6 linkages. Carrageenan is a linear sulphated polysaccharide extracted from red seaweeds. Guar gum, also called guaran, is a galactomannan extracted from guar beans. Pectin is a heteropolysaccharide derived from the cell wall of plants. Xanthan gum is a long chain polysaccharide composed of the sugars glucose, mannose, and glucuronic acid. Sodium alginate is a hydrocolloid composed of the sodium salt of two sugar uronates, mannuronic acid and guluronic acid. Arabinoxylan is a heteropolysaccharide that consist of arabinofuranose residues attached to xylopyranose polymeric backbone chains. Cellulose is a linear glucose polymer with beta-1,4 linkages. Carboxymethyl cellulose is a cellulose derivative with carboxymethyl groups ($—CH_2—COOH$) bound to some of the hydroxyl groups of the glucopyranose monomers that make up the cellulose backbone. Xylans are highly complex heteropolysaccharides found the cell walls of plants and in some algae. Beta-glucan is a glucose polymer with beta-1, 3/1,6-linkages. Curdlan, or beta-1,3-glucan, is a glucose polymer with beta-1.3 linkages. Gum arabic is a mixture of saccharides and glycoproteins extracted from the acacia tree. Locust bean gum is a galactomannan vegetable gum extracted from the seeds of the Carob tree. Hyaluronic acid is a non-sulphated member of the family of glycosaminoglycans. Gelatine is a protein produced by partial hydrolysis of collagen extracted from the connective tissues of many animals. Soy protein is the storage protein held in discrete particles called protein bodies of the soya bean.

Hyaluronan (also called hyaluronic acid or hyaluronate) is a non-sulfated glycosaminoglycan. Hyaluronan is a polymer of disaccharides, themselves composed of D-glucuronic acid and D-N-acetylglucosamine, linked together via alternating β-1,4 and beta-1,3 glycosidic bonds. Hyaluronan can be 25,000 disaccharide repeats in length. Polymers of hyaluronan can range in size from 5,000 to 20,000,000 Da in vivo. Hyaluronic acid is naturally found in many tissues of the body, such as skin, cartilage, and the vitreous humor. It is therefore compatible to biomedical applications involving these tissues. In skin tissue hyaluronic acid is the jelly like substance that fills the space between the collagen and elastin fibers in the skin and provides a transport mechanism of essential nutrients from the bloodstream to living skin cells. Its water holding capacity hydrates the skin. (Block and Bettelheim, 1970, Goa and Benfield, 1994) and acts as a cushioning and lubricating agent against mechanical and chemical damage. Because of its water retention properties and its ability to support growth of fibroblasts and keratinocytes (Liu, 2007) in the preparation of artificial skin for wound healing, the importance of hyaluronic acid has further augmented its use in the above mentioned agglomerated colostrum cream.

Beta-glucan is a naturally derived polysaccharide that has been studied for its anti-tumor and immune stimulating properties. It exert potent effects on the immune system—stimulating anti-tumour and anti-microbial activity, for example by binding to receptors on macrophages and other white blood cells and activating them (Gu et al., 2005)

Xanthan gum is a polysaccharide. The backbone of the polysaccharide chain consists of two beta-D-glucose units linked through the 1 and 4 positions. The side chain consists of two mannose and one glucuronic acid, so the chain consists of repeating modules of five sugar units. The side chain is linked to every other glucose of the backbone at the 3 position. About half of the terminal mannose units have a pyruvic acid group linked as a ketal to its 4 and 6 positions. The other mannose unit has an acetyl group at the 6 positions. Two of these chains may be aligned to form a double helix, giving a rather rigid rod configuration that accounts for its high efficiency as a viscosifier of water. The molecular weight of xanthan varies from about one million to 50 million depending upon how it is prepared.

The chemical compound sodium alginate is the sodium salt of alginic acid. Its empirical chemical formula is $NaC_6H_7O_6$. Its form as a gum, when extracted from the cell walls of brown algae, is used by the foods industry to increase viscosity and as an emulsifier. It is also used in indigestion tablets and the preparation of dental impressions. Sodium alginate has no discernible flavor. Alginic acid (algin, alginate) is a viscous gum that is abundant in the cell walls of brown algae. Chemically, it is a linear copolymer with homopolymeric blocks of (1-4)-linked beta-D-mannuronate (M) and its C-5 epimer alpha-L-guluronate (G) residues, respectively, covalently linked together in different sequences or blocks. The monomers can appear in homopolymeric blocks of consecutive G-residues (G-blocks), consecutive M-residues (M-blocks), alternating M and G-residues (MG-blocks) or randomly organized blocks.

Xanthan gum and sodium alginate are used in drug delivery systems where they are known to positively modify the physiochemical as well as drug release properties of the drug compositions (Pongjanyakul and Puttipipatkhachorn, 2006).

In another embodiment the hydrocolloid is selected from the group consisting of agar/agar, starch and its derivatives, potato starch, carrageenan, xanthan gum, alginate, cellulose and its derivatives, carboxymethyl cellulose, chitin, xylan, curdlan, beta-glucan, gum Arabic, hyaluronic acid, gelatine and soya protein. In yet another embodiment the hydrocolloid is selected from the group consisting of guar gum, pectin and its derivatives, xanthan gum, alginate, arabinoxylan, cellulose and its derivatives, carboxymethyl cellulose, chitin, xylan, beta-glucan, gum Arabic, hyaluronic acid, and gelatine.

In one embodiment said at least one agent of the composition is selected from the group consisting of xanthan gum, sodium alginate, beta-glucan and hyaluronic acid, or derivatives thereof. In another embodiment said at least one agent is selected from the group consisting of xanthan gum, sodium alginate and beta-glucan or derivatives thereof. Said at least one agent is selected from the group consisting of xanthan gum, beta-glucan and hyaluronic acid or derivatives thereof, or selected from the group consisting of xanthan gum, sodium alginate and hyaluronic acid or derivatives thereof, or selected from the group consisting of sodium alginate, beta-glucan and hyaluronic acid or derivatives thereof, or selected from the group consisting of xanthan gum and beta-glucan or derivatives thereof, or selected from the group consisting of xanthan gum and sodium alginate or derivatives thereof, or selected from the group consisting of xanthan gum and hyaluronic acid or derivatives thereof, or selected from the group consisting of sodium alginate and beta-glucan or derivatives thereof, selected from the group consisting of sodium alginate and hyaluronic acid or derivatives thereof, selected from the group consisting of beta-glucan and hyaluronic acid or derivatives thereof. In one embodiment said at least one agent of the composition is xanthan gum or derivatives thereof. Alternatively, said at least one agent is sodium alginate or derivatives thereof. However, in one embodiment the at least one agent is beta-glucan or derivatives thereof. In a preferred embodiment of the present invention said at least one agent is hyaluronic acid or derivatives thereof.

In one embodiment the composition of the present invention comprises bioconjugates of colostrum and one or more of said agents, wherein the amount of said agent is between 0.01% to 20% (w/w) of the total amount of colostrum. In another embodiment of the present invention, the composition comprise bioconjugates of colostrum and one or more of said agents, wherein the amount of said agent is between 0.01% to 10% (w/w) of the total amount of colostrum. In another embodiment the composition of the present invention comprises bioconjugates of colostrum and one or more of said agents, wherein the amount of said agent is in the range 1% to 10% (w/w) of the total amount of colostrum. In yet another embodiment the composition of the present invention comprises bioconjugates of colostrum and one or more of said agents, wherein the amount of said agent is in the range 2% to 6% (w/w) of the total amount of colostrum. In a further embodiment the composition of the present invention comprises bioconjugates of colostrum and one or more of said agents, wherein the amount of said agent is in the range 4% and 5% (w/w) of the total amount of colostrum.

In a preferred embodiment the composition of the present invention comprises bioconjugates of colostrum and hyaluronic acid or derivatives thereof, wherein the amount of hyaluronic acid or derivatives thereof is at least 4.5% (w/w) of the total amount of colostrum, and wherein the colostrum of the present invention is whole colostrum without fat and/or lactose of bovine origin, collected up to 48 hours of delivery, which was originally freeze-dried and wherein the amount of colostrum is in the range 5% to 30% (w/w) of the total composition.

Bioconjugation

Bioconjugation is the process of coupling one or more biomolecules together in a covalent linkage. Common types of bioconjugation chemistry are amine coupling of lysine amino acid residues (typically through amine-reactive succinimidyl esters), sulfhydryl coupling of cysteine residues (via a sulfhydryl-reactive maleimide), and photochemically initiated free radical reactions, which have broader reactivity. The product of a bioconjugation reaction is a bioconjugate.

In the present invention the bioconjugation is the coupling of a hydrocolloid to colostrum and/or the coupling of colostrum components to colostrum components. The term bioconjugation is used herein interchangeably with the term agglomeration, conglomeration or aggregation.

The bioconjugated composition of the present invention has several advantages compared to a similar composition that is not bioconjugated. The size of the bioconjugates facilitates penetration of the active components into the skin and direct cellular processes within the skin. In addition, the bioconjugated composition has increased immunostimulatory and anti-inflammatory effects, compared to similar compositions not comprising bioconjugates (Ex. 14, FIGS. 11-18). Furthermore, the composition comprising bioconjugated particles has superior properties regarding degradation (Ex. 9, FIG. 2) and in vivo clearance, compared to similar compositions not comprising bioconjugates.

The amount of bioconjugated colostrum in the present invention, i.e. the amount of colostrum in the bioconjugates, compared to of the total amount of colostrum, is calculated as described in Example 7 herein below. In one embodiment of the present invention, the amount of colostrum in the bioconjugates is 30% to 100% (w/w) of the total amount of colostrum, for example 40% to 100% (w/w), such as 50% to 100% (w/w), for example 60% to 100% (w/w), 70% to 100% (w/w), such as 80% to 100% (w/w), for example 90% to 100% (w/w). In a preferred embodiment, the amount of bioconjuagted colostrum is 90-100% (w/w) of the total amount of colostrum.

Cross-Linking

Cross-links are chemical bonds that link one polymer chain to another, and can be covalent or ionic in nature. Polymer chains can refer to synthetic polymers or natural polymers (such as proteins, polysaccharides etc.). The cross-linking agent (or cross-linker) refers to the compound that mediates the chemical bonding of two or more polymer chains. Alternatively, bonds are formed within one polymer chain. It is appreciated that the cross linking thus occurs between two or more polymer chains, and/or within one polymer chain.

According to the present invention, cross-linking of the composition comprising colostrum and at least one agent results in bioconjugation of these components.

In one embodiment of the present invention the cross-linker is selected from EGS (Ethylene glycol bis[succinimidylsuccinate]), Sulfo EGS (Ethylene glycol bis[sulfosuccinimidylsuccinate]), C6-SANH(C6-succinimidyl 4-hydrazinonicotinate acetone hydrazone), SANH (succinimidyl 4-hydrazinonicotinate acetone hydrazone), C6-SFB (C6-succinimidyl 4-formylbenzoate), BSOCOES (Bis[2-(succinimidyloxycarbonyloxy)ethyl]sulfone), DSP (Dithiobis[succinimidyl propionate]), DTSSP (3,3'-Dithiobis[sulfosuccinimidylpropionat]), DTBPD (Dimethyl 3,3''-dithiobispropionimidate.2HCl), DSS (Disuccinimidyl suberate), BS (Bis[sulfosuccinimidyl] suberate), DMS (Dimethyl Suberimidate.2HCl), DMP (Dimethyl pimelimidate.2HCl), DMA (Dimethyl adipimidate.2HCl), SHTH (Succinimidyl 4-hydrazidoterephthalate hydrochloride), DSG (Disuccinimidyl glutarate), MSA (Methyl N-succinimidyl adipate), DST (Disuccinimidyl tartarate), SFB (Succinimidyl 4-formylbenzoate), DFDNB (1,5-Difluoro-2,4-dinitrobenzene), DSP (Dithiobis[succinimidyl propionate]), DTSSP (3,3'-Dithiobis[sulfosuccinimidylpropionate]), EDC/NHS, glutaraldhyde, dihydroxyacetone, phenyl azide, tyrosinase and/or transglutaminase.

In a preferred embodiment of the present invention, the cross-linking agent is selected from EDC/NHS or derivatives thereof, glutaraldehyde or derivatives thereof, transglutaminase or derivatives thereof, tyrosinase or derivatives thereof, and/or dihydroxyacetone or derivatives thereof.

In preferred embodiments the cross-linking agent is dihydroxyacetone or derivatives thereof, the cross-linking agent is EDC/NHS or derivatives thereof, the cross-linking agent is glutaraldehyde or derivatives thereof, the cross-linking agent is transglutaminase or derivatives thereof, the cross-linking agent is glutaraldehyde or derivatives thereof, the cross-linking agent is transglutaminase or derivatives thereof, the cross-linking agent is tyrosinase or derivatives thereof.

Particles of Bioconjugates

The present invention relates to bioconjugated compositions, wherein said bioconjugated compositions comprise particles. The composition of the present invention comprises bioconjugates of colostrum components and hydrocolloids, and/or bioconjugates of colostrum components and colostrum components, wherein said bioconjugates is in the form of particles. In a preferred embodiment of the present invention, these particles are globular and/or spherical in shape, and are individual particles and/or clusters of particles.

The particles of the bioconjugates may be of equal or different sizes. In one embodiment of the present invention, these particles have diameters in the range of 0.1 nm to 1.0 µm. In another embodiment of the present invention, the particles have diameters in the range of 1 nm to 500 nm, for example 5 nm to 400 nm, such as 10 nm to 350 nm, for example 20 nm to 300 nm, 30 nm to 250 nm, such as 40 nm to 200 nm, 50 nm to 170 nm, for example 60 nm to 150 nm or 75 nm to 100 nm.

In a preferred embodiment of the present invention, the particles have diameters in the range of 10 nm to 300 nm. In another preferred embodiment of the present invention, the particles have diameters in the range of 50 nm to 150 nm (FIG. 1A). In a further preferred embodiment of the present invention, the particles have diameters in the range of 30 nm to 60 nm (FIG. 1B).

Composition

In one embodiment, the composition of the present invention comprises whole colostrum without fat and/or lactose of bovine origin, collected up to 48 hours of delivery, which was originally freeze-dried and wherein the amount of colostrum is in the range of 1% to 95% (w/w) of the total composition, and at least one hydrocolloid agent wherein the amount of said agent is between 0.01% to 20% (w/w) of the total amount of colostrum and wherein the hydrocolloid agent is hyaluronic acid, and wherein the composition is bioconjugated and wherein the amount of colostrum in the bioconjugates is in the range of 30% to 100% (w/w) of the total amount of colostrum, and wherein the diameters of the bioconjugated particles (bioconjugates) is in the range of 10 nm to 300 nm.

In a preferred embodiment, the composition of the present invention comprises whole colostrum without fat and/or lactose of bovine origin, collected up to 48 hours of delivery, which was originally freeze-dried and wherein the amount of colostrum is in the range of 5% to 30% (w/w) of the total composition, and at least one hydrocolloid agent wherein the amount of said agent is between 0.01% to 10% (w/w) of the total amount of colostrum and wherein the hydrocolloid agent is hyaluronic acid, and wherein the composition is bioconjugated, and wherein the amount of colostrum in the bioconjugates is in the range of 90% to 100% (w/w) of the total amount of colostrum, and wherein the diameters of the bioconjugated particles (bioconjugates) is in the range of 30 nm to 60 nm and/or 50 nm to 150 nm.

Immune Modulation and Growth Modulation

The term "immuno modulation" as used herein refers to the process wherein an immune response is either suppressed, partly or completely, or triggered or induced or enhanced. In the first case the immune modulation results in immunosuppression, in the latter case the immune modulation results in immunostimulation. The composition of the present invention has immune modulatory properties. In one embodiment the composition of the present invention has an immunostimulatory effect or property. In another embodiment the composition of the present invention has an immunosuppressive effect or property.

Likewise, the term "growth-modulation" as used herein refers to the process wherein the cell proliferation is either suppressed, partly or completely, or where cell proliferation is induced or enhanced or promoted. In the first case the growth modulation results in growth suppression, in the latter case the growth modulation results in growth stimulation. The composition of the present invention has growth modulatory properties. In one embodiment the composition of the present invention has an growth stimulatory effect or property. In another embodiment the composition of the present invention has a growth suppressive effect or property.

Administration Forms

The main routes of drug delivery, in the treatment method are intravenous, oral, and topical, as will be described below. Other drug-administration methods, such as subcutaneous injection or via inhalation, which are effective to deliver the drug to a target site or to introduce the drug into the bloodstream, are also contemplated.

The mucosal membrane to which the pharmaceutical preparation of the invention is administered may be any mucosal membrane of the mammal to which the biologically active substance is to be given, e.g. in the nose, vagina, eye, mouth, genital tract, lungs, gastrointestinal tract, or rectum, preferably the mucosa of the nose, mouth or vagina.

Compositions of the invention may be administered parenterally, that is by intravenous, intramuscular, subcutaneous intranasal, intrarectal, intravaginal or intraperitoneal administration. The subcutaneous and intramuscular forms of parenteral administration are generally preferred. Appropriate dosage forms for such administration may be prepared by conventional techniques. The compositions may also be administered by inhalation that is by intranasal and oral inhalation administration. Appropriate dosage forms for such administration, such as an aerosol formulation or a metered dose inhaler, may be prepared by conventional techniques.

The compositions according to the invention may be administered with at least one other compound. The compounds may be administered simultaneously, either as separate formulations or combined in a unit dosage form, or administered sequentially.

Dosing Regimes

The dosage requirements will vary with the particular drug composition employed, the route of administration and the particular subject being treated. Ideally, a patient to be treated by the present method will receive a pharmaceutically effective amount of the composition in the maximum tolerated dose, generally no higher than that required before drug resistance develops.

For all methods of use disclosed herein for the compositions, the daily oral dosage regimen will preferably be from about 0.01 to about 80 mg/kg total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a composition or a pharmaceutically acceptable salt thereof will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a composition or a pharmaceutically acceptable salt thereof given per day for a defined number of days, can be ascertained by those skilled in the art using conventional course of treatment determination tests.

The term "unit dosage form" as used herein refers to physically discrete units suitable as unitary dosages for human and animal subjects, each unit containing a predetermined quantity of a composition, alone or in combination with other agents, calculated in an amount sufficient to produce the desired effect in association with a pharmaceutically acceptable diluent, carrier, or vehicle. The specifications for the unit dosage forms of the present invention depend on the particular composition or compositions employed and the effect to be achieved, as well as the pharmacodynamics associated with each composition in the host. The dose administered should be an "effective amount" or an amount necessary to achieve an "effective level" in the individual patient.

Since the "effective level" is used as the preferred endpoint for dosing, the actual dose and schedule can vary, depending on the individual differences in pharmacokinetics, drug distribution, and metabolism. The "effective level" can be defined, for example, as the blood or tissue level desired in the patient that corresponds to a concentration of one or more compositions according to the invention.

Pharmaceutical compositions containing a composition of the present invention may be prepared by conventional techniques, e.g. as described in Remington: The Science and Practice of Pharmacy 1995, edited by E. W. Martin, Mack Publishing Company, 19th edition, Easton, Pa. The compositions may appear in conventional forms, for example capsules, tablets, aerosols, solutions, suspensions or topical applications.

Formulations

Whilst it is possible for the compositions or salts of the present invention to be administered as the raw chemical, it is preferred to present them in the form of a pharmaceutical formulation. Accordingly, the present invention further provides a pharmaceutical formulation, for medicinal application, which comprises a composition of the present invention or a pharmaceutically acceptable salt thereof, as herein defined, and a pharmaceutically acceptable carrier therefore.

The compositions of the present invention may be formulated in a wide variety of oral administration dosage forms. The pharmaceutical compositions and dosage forms may comprise the compositions of the invention or its pharmaceutically acceptable salt or a crystal form thereof as the active component. The pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, lubricants, suspending agents, binders, preservatives, wetting agents, tablet disintegrating agents, or an encapsulating material.

Preferably, the composition will be about 0.5% to 75% by weight of a composition or compositions of the invention, with the remainder consisting of suitable pharmaceutical excipients. For oral administration, such excipients include pharmaceutical grades of mannitol, lactose, starch, magnesium stearate, sodium saccharine, talcum, cellulose, glucose, gelatin, sucrose, magnesium carbonate, and the like.

In powders, the carrier is a finely divided solid which is a mixture with the finely divided active component. In tablets, the active component is mixed with the carrier having the necessary binding capacity in suitable proportions and compacted in the shape and size desired. The powders and tablets preferably contain from one to about seventy percent of the active composition. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active composition with encapsulating material as carrier providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Also included are solid form preparations which are intended to be converted, shortly before use, to liquid form preparations for oral administration. Such liquid forms include solutions, suspensions, and emulsions. These preparations may contain, in addition to the active component, colorants, flavours, stabilizers, buffers, artificial and natural sweeteners, dispersants, thickeners, suspensing and emulsifying agents, and the like.

Other forms suitable for oral administration include liquid form preparations including emulsions, syrups, elixirs, aqueous solutions, aqueous suspensions, toothpaste, gel dentrifrice, chewing gum, or solid form preparations which are intended to be converted shortly before use to liquid form preparations. Emulsions may be prepared in solutions in aqueous propylene glycol solutions or may contain emulsifying agents such as lecithin, sorbitan monooleate, or acacia. Aqueous solutions can be prepared by suspending or mixing the active component in water and adding suitable colorants, flavors, stabilizing and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include suspensions and emulsions, and may contain, in addition to the active component, colorants, flavors, stabilizers, buffers, artificial and natural sweeteners, dispersants, thickeners, and the like.

The compositions of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

Oils useful in parenteral formulations include petroleum, animal, vegetable, or synthetic oils. Specific examples of oils useful in such formulations include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides; (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-.beta.-aminopropionates, and 2-alkyl-imidazoline quaternary ammonium salts, and (e) mixtures thereof.

The parenteral formulations typically will contain from about 0.5 to about 25% by weight of the active ingredient in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

The compositions of the invention can also be delivered topically. Regions for topical administration include the skin surface and also mucous membrane tissues of the vagina, rectum, nose, mouth, and throat. Compositions for topical administration via the skin and mucous membranes should not give rise to signs of irritation, such as swelling or redness.

The topical composition may include a pharmaceutically acceptable carrier adapted for topical administration. Thus, the composition may take the form of a suspension, solution, ointment, lotion, sexual lubricant, cream, foam, aerosol, spray, suppository, implant, inhalant, tablet, capsule, dry powder, syrup, balm or lozenge, for example. Methods for preparing such compositions are well known in the pharmaceutical industry.

The compositions of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or colouring agents. Formulations suitable for topical administration in the mouth include lozenges comprising active agents in a flavoured base, usually sucrose and acacia or tragacanth; pastilles comprising the active ingredient in an inert base such as gelatine and glycerin or sucrose and acacia; and mouthwashes comprising the active ingredient in a suitable liquid carrier.

Creams, ointments, gels, balms, or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan ester or a polyoxyethylene derivative thereof. Suspending agents such as natural gums, cellulose derivatives or inorganic materials such as silicaceous silicas, and other ingredients such as lanolin, may also be included.

Lotions according to the present invention include those suitable for application to the skin or eye. In a preferred embodiment the lotions of the present invention is for topical application to the skin. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil, jojoba, arachis oil, simmondsia chinensis oil, olea europaea fruit oil, aracis hypogae oil, prunus amygdalus dulcis oil.

In one embodiment of the present invention the composition is in the form of a lip balm, gel, mask, ointment, cream, lotion and/or shampoo.

Transdermal Delivery

The pharmaceutical agent-chemical modifier complexes described herein can be administered transdermally. Transdermal administration typically involves the delivery of a pharmaceutical agent for percutaneous passage of the drug into the systemic circulation of the patient. The skin sites include anatomic regions for transdermally administering the drug and include the forearm, abdomen, chest, back, buttock, mastoidal area, and the like.

Transdermal delivery is accomplished by exposing a source of the complex to a patient's skin for an extended period of time. Transdermal patches have the added advantage of providing controlled delivery of a pharmaceutical agent-chemical modifier complex to the body. See Transdermal Drug Delivery: Developmental Issues and Research Initiatives, Hadgraft and Guy (eds.), Marcel Dekker, Inc., (1989); Controlled Drug Delivery: Fundamentals and Applications, Robinson and Lee (eds.), Marcel Dekker Inc., (1987); and Transdermal Delivery of Drugs, Vols. 1-3, Kydonieus and Berner (eds.), CRC Press, (1987). Such dosage forms can be made by dissolving, dispersing, or otherwise incorporating the pharmaceutical agent-chemical modifier complex in a proper medium, such as an elastomeric matrix material. Absorption enhancers can also be used to increase the flux of the composition across the skin. The rate of such flux can be controlled by either providing a rate-controlling membrane or dispersing the composition in a polymer matrix or gel.

Passive Transdermal Drug Delivery

A variety of types of transdermal patches will find use in the methods described herein. For example, a simple adhesive patch can be prepared from a backing material and an acrylate adhesive. The pharmaceutical agent-chemical modifier complex and any enhancer are formulated into the adhesive casting solution and allowed to mix thoroughly. The solution is cast directly onto the backing material and the casting solvent is evaporated in an oven, leaving an adhesive film. The release liner can be attached to complete the system.

Alternatively, a polyurethane matrix patch can be employed to deliver the pharmaceutical agent-chemical modifier complex. The layers of this patch comprise a backing, a polyurethane drug/enhancer matrix, a membrane, an adhesive, and a release liner. The polyurethane matrix is prepared using a room temperature curing polyurethane prepolymer. Addition of water, alcohol, and complex to the prepolymer results in the formation of a tacky firm elastomer that can be directly cast only the backing material.

A further embodiment of this invention will utilize a hydrogel matrix patch. Typically, the hydrogel matrix will comprise alcohol, water, drug, and several hydrophilic polymers. This hydrogel matrix can be incorporated into a transdermal patch between the backing and the adhesive layer.

The liquid reservoir patch will also find use in the methods described herein. This patch comprises an impermeable or semipermeable, heat sealable backing material, a heat sealable membrane, an acrylate based pressure sensitive skin adhesive, and a siliconized release liner. The backing is heat sealed to the membrane to form a reservoir which can then be filled with a solution of the complex, enhancers, gelling agent, and other excipients.

Foam matrix patches are similar in design and components to the liquid reservoir system, except that the gelled pharmaceutical agent-chemical modifier solution is constrained in a thin foam layer, typically a polyurethane. This foam layer is situated between the backing and the membrane which have been heat sealed at the periphery of the patch.

For passive delivery systems, the rate of release is typically controlled by a membrane placed between the reservoir and the skin, by diffusion from a monolithic device, or by the skin itself serving as a rate-controlling barrier in the delivery system. See U.S. Pat. Nos. 4,816,258; 4,927,408; 4,904,475; 4,588,580, 4,788,062; and the like. The rate of drug delivery will be dependent, in part, upon the nature of the membrane. For example, the rate of drug delivery across membranes within the body is generally higher than across dermal barriers. The rate at which the complex is delivered from the device to the membrane is most advantageously controlled by the use of rate-limiting membranes which are placed between the reservoir and the skin. Assuming that the skin is sufficiently permeable to the complex (i.e., absorption through the skin is greater than the rate of passage through the membrane), the membrane will serve to control the dosage rate experienced by the patient.

Suitable permeable membrane materials may be selected based on the desired degree of permeability, the nature of the complex, and the mechanical considerations related to constructing the device. Exemplary permeable membrane materials include a wide variety of natural and synthetic polymers, such as polydimethylsiloxanes (silicone rubbers), ethylenevinylacetate copolymer (EVA), polyurethanes, polyurethane-polyether copolymers, polyethylenes, polyamides, polyvinylchlorides (PVC), polypropylenes, polycarbonates, polytetrafluoroethylenes (PTFE), cellulosic materials, e.g., cellulose triacetate and cellulose nitrate/acetate, and hydrogels, e.g., 2-hydroxyethylmethacrylate (HEMA).

Other items may be contained in the device, such as other conventional components of therapeutic products, depending upon the desired device characteristics. For example, the compositions according to this invention may also include one or more preservatives or bacteriostatic agents, e.g., methyl hydroxybenzoate, propyl hydroxybenzoate, chlorocresol, benzalkonium chlorides, and the like. These pharmaceutical compositions also can contain other active ingredients such as antimicrobial agents, particularly antibiotics, anesthetics, analgesics, and antipruritic agents.

The compositions of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The active composition may be formulated into a suppository comprising, for example, about 0.5% to about 50% of a composition of the invention, disposed in a polyethylene glycol (PEG) carrier (e.g., PEG 1000 [96%] and PEG 4000 [4%].

The compositions of the present invention may be formulated for vaginal administration. Pessaries, tampons, creams, gels, pastes, foams or sprays containing in addition to the active ingredient such carriers as are known in the art to be appropriate.

The compositions of the present invention may be formulated for nasal administration. The solutions or suspensions are applied directly to the nasal cavity by conventional means, for example with a dropper, pipette or spray. The formulations may be provided in a single or multidose form. In the latter case of a dropper or pipette this may be achieved by the patient administering an appropriate, predetermined volume of the solution or suspension. In the case of a spray this may be achieved for example by means of a metering atomizing spray pump.

The compositions of the present invention may be formulated for aerosol administration, particularly to the respiratory tract and including intranasal administration. The composition will generally have a small particle size for example of the order of 5 microns or less. Such a particle size may be obtained by means known in the art, for example by micronization. The active ingredient is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the composition in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatine or blister packs from which the powder may be administered by means of an inhaler.

When desired, formulations can be prepared with enteric coatings adapted for sustained or controlled release administration of the active ingredient.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Pharmaceutically Acceptable Salts

Pharmaceutically acceptable salts of the instant compositions, where they can be prepared, are also intended to be covered by this invention. These salts will be ones which are acceptable in their application to a pharmaceutical use. By that it is meant that the salt will retain the biological activity of the parent composition and the salt will not have untoward or deleterious effects in its application and use in treating diseases.

Pharmaceutically acceptable salts are prepared in a standard manner. If the parent composition is a base it is treated with an excess of an organic or inorganic acid in a suitable solvent. If the parent composition is an acid, it is treated with an inorganic or organic base in a suitable solvent.

The compositions of the invention may be administered in the form of an alkali metal or earth alkali metal salt thereof, concurrently, simultaneously, or together with a pharmaceutically acceptable carrier or diluent, especially and preferably in the form of a pharmaceutical composition thereof, whether by oral, rectal, or parenteral (including subcutaneous) route, in an effective amount.

Examples of pharmaceutically acceptable acid addition salts for use in the present inventive pharmaceutical composition include those derived from mineral acids, such as hydrochloric, hydrobromic, phosphoric, metaphosphoric, nitric and sulfuric acids, and organic acids, such as tartaric, acetic, citric, malic, lactic, fumaric, benzoic, glycolic, gluconic, succinic, p-toluenesulphonic acids, and arylsulphonic, for example.

The Pharmaceutical Carrier

The term "pharmaceutically acceptable" refers to molecular entities and compositions that do not produce an allergic, toxic, or otherwise adverse reaction when administered to an animal, particularly a mammal, and more particularly a human. Pharmaceutical acceptable carriers include any and all solvents, dispersion media, coatings, antibacterial and antifungal agents, stabilizers, isotonic and absorption delaying agents and the like. The use of such media and agents for pharmaceutical active substances is well known in the art.

Illustrative solid carriers include lactose, terra alba, sucrose, talc, gelatin, agar, pectin, acacia, magnesium stearate, stearic acid and the like. A solid carrier can include one or more substances which may also act as flavouring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions, and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, chitin, polyvinylpyrrolidine, low melting waxes and ion exchange resins.

Illustrative liquid carriers include syrup, peanut oil, olive oil, water, etc. Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavouring agents, suspending agents, thickening agents, colours, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carders are useful in sterile liquid form compositions for parenteral administration. The liquid carrier for pressurized compositions can be halogenated hydrocarbon or other pharmaceutically acceptable propellant. Liquid pharmaceutical compositions which are sterile solutions or suspensions can be utilized by, for example, intramuscular, intraperitoneal or subcutaneous injection. Sterile solutions can also be administered intravenously. The composition can also be administered orally either in liquid or solid composition form.

The carrier or excipient may include time delay material well known to the art, such as glyceryl monostearate or glyceryl distearate along or with a wax, ethylcellulose, hydroxypropylmethylcellulose, methylmethacrylate and the like. When formulated for oral administration, 0.01% Tween 80 in PHOSAL PG-50 (phospholipid concentrate with 1,2-propylene glycol, A. Nattermann & Cie. GmbH) has been recognized as providing an acceptable oral formulation for other compounds, and may be adapted to formulations for various compositions of this invention.

"Combination therapy" (or "co-therapy") includes the administration of the composition of the invention and at least a second component as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Immune Stimulating and Anti-Inflammatory Properties

Without being bound by theory, it is believed that an adaptive immune response relies on special cells such as T-cells, B-cells and macrophages. In the presence of pathogenic viruses/cells (infection), Type 1 helper cells (Th1-type cells) are activated and release Th-1 type specific cytokines such as interleukin-2 (IL-2) and Interferon-gamma (IFN-gamma). IFN-gamma then induces a high output of toxic reactive oxygen species (ROS) in macrophages as well as induction of enzymes such as indole amine 2,3 dioxygenase (IDO) and GTP cyclohydrolase I (GCH). These enzymes are responsible for the conversion of tryptophan (trp) to knyurinine (kyn) and neopterin. These are directed to destroy vital structures such as lipids and proteins and to inhibit proliferation of cells and pathogens. ROS also trigger redox sensitive intracellular signal transduction cascades involving Nuclear factor-kappa-B; (NF-kappa-B), which in turn accelerates the production of proinflammatory cytokines such as Tumor necrosis factor-alpha (TNF-alpha). During prolonged periods of Th1-type activation, for example in chronic infections, there is a continuous production of ROS which in turn amplifies the release of proinflammatory cytokines and also leads to the depletion of antioxidation pools and hence emergence of oxidative stress. The determination of cytokines is especially limited due to their short life in the circulation. Activated Th-1 type immune response can be easily sensitively detected when secondary messengers of IFN-gamma are monitored.

During Th-1 type immune response, activated T-cells release large amounts of cytokines such as IL-2 or IFN-gamma, which mediate pro-inflammatory functions critical for the development of cell-mediated immune responses. Besides other pathways, T-cell derived IFN-gamma induces also activation of the enzyme indoleamine 2,3-dioxygenase (IDO) in macrophages, that converts tryptophan into N-formylkynurenine, which subsequently is deformylated to kynurenine (Wirleitner and others 2003). IDO plays a central role in the suppression of intracellular bacteria and viruses during an antimicrobial immune response, as ongoing tryptophan degradation limits protein biosynthesis due to deprivation of this essential amino acid (Pfefferkorn 1986; Ozaki and others 1988). In diseases which are associated with inflammation and immune activation, accelerated tryptophan degradation manifests in decreased serum tryptophan concentrations and increased kynurenine to tryptophan ratios (kyn/trp), as a measure of IDO activity. In parallel to tryptophan degradation, IFN-gamma also stimulates formation of neopterin, via induction of the enzyme guanosine-triphosphate-(GTP)-cyclohydrolase, representing another marker for the activation of the T cell-macrophage axis in humans (Huber and others 1984; Wirleitner and others 2003). Due to the short half life of cytokines whose measurment is often challenging, the measurement of IDO activity and formation of neopterin provides a robust approach to evaluate the modulation of a Th-1 type immune response in human PBMC.

In course of disease with an activated cellular immune esponse, there is concurrently an increase in the production of neopterin and degradation of tryptophan to knyurinine. Available data suggests that by means of neopterin and kyn/trp measurements a sensitive monitoring of the immune response is feasible which in the course of chronic disease allows conclusions about oxidative stress in in patients.

Besides measurement of neopterin production and tryptophan degradation gives a direct insight into interplay between T-cells and macrophages and also are directly related to the pathogenesis of diseases in which inflammatory processes are involved.

The antiinflammatory as well as antioxidative properties of compounds which are known or claim to be antiinflammatory and/or antioxidative can thus be easily be measured by monitoring the decrease in neopterin production and the concomitant increase in the kyn/trp ratio in blood cells stimulated by mitogens such as concavalin A or phytohemaggluttinin in vitro.

The immunstimulatory and anti-inflammatory properties of composition of the present invention are described in Examples 14 and 16 and FIGS. 11-23.

Growth Stimulating Properties

One of the earliest repair responses following injury to tissue is the migration of surviving cells and their proliferation over any denuded area to re-establish epithelial integrity. Since it is extremely difficult to study this effect inside a human or animal, cell culture models are commonly used as surrogate markers of this pro-migratory response.

Cell proliferation assays were performed using well established methods (Nakayama et al., 1997) using Alamar blue (Invitrogen, Paisley, UK) as per manufacturers instructions measuring the change in absorbance. For the proliferation assays, the human colonic carcinoma cell line HT29 cells were used. Cell viability, determined by the ability to exclude 0.2% trypan blue, was greater than 90% in all experiments.

Briefly, cells were seeded at 2000 cells/well and grown in DMEM containing glutamine and 10% foetal calf serum in 96 well plates overnight. The following day, cells were washed with DMEM alone and incubated with 1, 5 or 10 mg/ml colostrum protein (v/v) preparation with or without Euxyl or with 1%, 0.3% or 0.06% Euxyl (concentrations equivalent to those found in the samples containing Euxyl) and incubated under serum starved conditions for 24 hours. Cells incubated in DMEM+10% FCS were used as a positive control whereas cells incubated in DMEM alone were used as a negative control. The following day Alamar blue was added to each well and change in absorbance at 570 nm was determined after 3-5 hours (Ex. 15, FIG. 3).

Proteolytic Stability Properties

Protelytic stability is used to describe the resistance of a given protein toward proteolysis, i.e. hydrolysis of the peptide (amide) bonds in the protein or peptide. In particular, proteolytic stability refers to the resistance toward the action of proteolytic enzymes, also known as proteases, i.e. enzymes that catalyzes the hydrolysis of the protein or peptide. In one embodiment of the present invention, the agglomerated or bioconjugated colostrum and said at least one agent has increased stability towards acid hydrolysis by proteases, as compared to agglomerated colostrum without said at least one agent. In another embodiment the bioconjugated composition of the present invention has increased proteolytic stability compared to an alternative composition comprising colostrum and/or said at least one agent, wherein said alternative composition is non-bioconjugated. In a preferred embodiment the said at least one agent is hyaluronic acid, and the bioconjugated colostrum or part thereof and hyaluronic acid is resistant to proteolysis at pH 5 for at least 24 hours (Ex. 9, FIG. 2).

Method of Preparation

In one aspect the present invention relates to a method for preparation of the composition described herein, comprising the steps of a) providing colostrum or part thereof, b) providing at least one agent, c) mixing said colostrum or part thereof and said at least one agent, d) providing at least one cross-linking agent, e) mixing said colostrum or part thereof, said at least one agent and said at least one cross-linking agent, f) obtaining a bioconjugate. Step e) is equivalent to the bioconjugation of the composition of the present invention. Step f) is equivalent to obtaining a bioconjugated composition. In one embodiment the bioconjugation is conducted in a buffer with acidity in the range of pH 6.0-8.0, however, a preferred range is pH 7.0-7.5. In the bioconjugation process of step e), the bioconjugation is stirred at a velocity in the range of 300 rpm-800 rpm in the presence of buffer. The bioconjugation is conducted in the buffer at a temperature in the range of 2° C.-45° C., however, a preferred temperature is in the range 20° C.-35° C.

The bioconjugation of the composition is obtainable by the aid of a cross-linking agent not limited to the cross-linkers listed elsewhere herein. The cross-linking agent may for example be selected from EDC/NHS or derivatives thereof, transglutaminase or derivatives thereof, tyrosinase or derivatives thereof, and/or dihydroxyacetone or derivatives thereof. Alternatively, the cross-linking agent is selected from aryl azides and/or polyphenol oxidases or derivatives thereof as described elsewhere herein. It is within the scope of the present invention to use a combination of two or more cross-linking agents selected from the listed agents in the method. In a preferred embodiment the cross-linker used in the method is EDC/NHS, or DHA.

In one embodiment the colostrum and at least one agent is dissolved separately prior to step c) mixing said colostrum and said at least one agent.

The mixing of the colostrum and the at least one agent and at least one cross-linking agent of step e) is in one embodiment combined with the stirring of the mixture in order to obtain particles of desired sizes. The stirring is conducted at 200 rpm to 1000 rpm, 300 rpm-800 rpm, preferably 400 rpm or 500 rpm.

It is appreciated that one aspect of the present invention relates to a composition obtainable by the method of preparation as described herein.

Uses

In one embodiment, the present invention relates to a composition for use as a medicament. In another embodiment, the present invention comprises a pharmaceutical composition and/or compositions for the treatment of skin diseases and/or skin conditions. For example one aspect relates to a pharmaceutical composition comprising the composition as described herein. In a preferred embodiment, the present invention comprises a pharmaceutical composition further comprising a pharmaceutically and/or physiologically acceptable carrier for the treatment of skin diseases and/or skin conditions.

A carrier may facilitate the transport of the ingredients of said composition to the site of action, e.g. covalently bound either directly or via a chemical linker. Effective carriers include proteins such as albumins, and/or peptides and polysaccharides such as aminodextran. A carrier may also transport the ingredients of said composition noncovalently bound or by encapsulation, such as within a liposome vesicle or other bio-vesicles.

The skin diseases and/or skin conditions that can be treated by the composition and/or pharmaceutical composition of the present invention is selected from the group consisting of solar eczema, eczemas of unknown aetiology, rashes, itchy skin conditions, irritated redness, ichtyosis, vitiligo, psoriasis, wounds, postoperative wounds, bite marks, chaps, sores, diabetic sores, lip sores, cracked lips, scars, cellulite, skin conditions caused by bacteria, skin conditions caused by viruses, skin conditions caused by fungus, skin conditions caused by insects, in particular mosquiotos, skin conditions caused by plants, in particular hogweeds and/or nettles, skin cancer, acne, pimples, impetigo, scabies, sunburn, warts, fifth disease, tinea, herpes, ulcers, pruritus, rosen, erysipelas, skin diseases due to absorption of compounds through the skin, bed sore, epidermolysis bullosis, blepharitis, atopic dermatitis, cold sores and boil. It is within the scope of the present invention that any of the listed skin diseases and/or skin conditions form each their separate embodiment, thus, the skin disease and/or skin conditions of the present invention is any of solar eczema, eczemas of unknown aetiology, rashes, itchy skin conditions, irritated redness, ichtyosis, vitiligo, psoriasis, wounds, postoperative wounds, sores, diabetic sores, lip sores, cracked lips, skin conditions caused by bacteria, skin conditions caused by viruses, skin conditions caused by fungus, skin conditions caused by insects, skin conditions caused by plants, skin cancer, acne, impetigo, scabies, sunburn, warts, fifth disease, tinea, herpes, ulcers, pruritus, skin diseases due to absorption of compounds through the skin, bed sore, epidermolysis bullosis, blepharitis, atopic dermatitis, cold sores or boil.

Eczema, also known as eczematous dermatitis, including rashes, itchy skin conditions, cracks and irritated redness are all conditions characterized by inflammation of the upper layers of the skin. Symptoms include skin edema, itching and dryness, crusting, flaking, blistering, cracking, oozing, and/or even bleeding.

Sores are sites of delayed healing characterized by loss of integrity in the involved area. Sores may be caused by, or accompanied by infection by bacteria, fungus and/or viruses. One example is bed sores. Another example is cold sores or genital herpes blisters caused by Herpes virus.

Skin diseases and skin conditions caused by viruses comprises skin conditions such as cold sores whichare small, painful, fluid-filled blisters or sores that appear on the lips, mouth, or nose that are caused by a virus. Skin conditions caused by virus are also herpes which is caused by herpes simplex virus. Both strains of Herpes Simplex Virus (HSV-1 and HSV-2) cause the disease. Most common is "oral herpes", causing sores in the face and around the mouth. The second most common disease caused by HSV infects the genitalia, and is known as "herpes". But also other disorders such as herpetic whitlow, herpes gladiatorum, ocular herpes (keratitis), cerebral herpes infection encephalitis, Mollaret's meningitis, neonatal herpes, and possibly Bell's palsy are caused by herpes simplex viruses.

Ichtyosis, of which ichtyosis vulgaris by far is the most common type, is usually an inherited skin disease although an aquired type of ichtyosis also exists. Ichtyosis is characterized by causing dry, scaly skin. Symptoms are not very severe, usually mild itching and faint scaling of the skin.

Vitiligo is an inherited chronic skin disease characterized by loss of pigment. The symptoms include white patches on the skin and purple and/or golden brown patches on mucous membranes and around the eyes, nostrils and mouth.

Psoriasis is a chronic hyperproliferative inflammatory skin disease. The symptoms are the appearance of red scaly patches of inflammation and excessive skin production, known as psoriatic plaques, especially on elbows and knees. The patches tend to take a silvery-white appearance as skin accumulates at the site of the plaque formation.

Boil is a skin disease caused by the infection of hair follicles, thus resulting in the localized accumulation of pus and dead tissue.

The skin disease and/or skin condition which can be treated by the composition and/or pharmaceutical composition of the present invention is selected from the group consisting of solar eczema, eczemas of unknown aetiology, rashes, itchy skin conditions, irritated redness, psoriasis, wounds, postoperative wounds, sores, diabetic sores, lip sores, cracked lips, skin conditions caused by bacteria, skin conditions caused by viruses, skin conditions, skin conditions caused by fungus, skin conditions caused by insects, skin conditions caused by plants, acne, sunburn, warts, fifth disease, tinea, herpes, ulcers, pruritus, bed sore and cold sores.

In another embodiment the skin disease and/or skin condition which can be treated by the composition and/or pharmaceutical composition of the present invention is selected from the group consisting of eczemas of unknown aetiology, rashes, itchy skin conditions, irritated redness, psoriasis, wounds, postoperative wounds, sores, diabetic sores, skin conditions caused by bacteria, skin conditions caused by viruses, skin conditions caused by fungus, skin conditions caused by insects, skin conditions caused by plants, acne, herpes, pruritus and bed sore.

In preferred embodiments the compositions of the present invention is used for the treatment of itchy skin conditions, wounds, sores, eczemas and/or psoriasis. In an especially preferred embodiment the compositions of the present invention is used for the treatment of psoriasis.

The present invention consequently relates to the treatment of any of the skin diseases and/or skin conditions listed herein comprising administration of the composition of the present invention in a therapeutically effective amount to an animal in need thereof. Similarly, the composition may be used to treat a skin disease and/or a skin condition in an animal. The term 'animal' as used herein may be defined to include human, domestic or agricultural (cats, dogs, cows, sheep, horses, pigs, etc.) or test species such as mouse, rat, rabbit etc.

One aspect of the present invention relates to the use of the composition of the present invention for the manufacture of a medicament. In analogy, another aspect of the invention relates to use of the composition as a medicament. Furthermore the present invention also relates to a method of treatment of skin conditions comprising administration of the composition of the present invention in a therapeutically effective amount to an animal in need thereof.

For treatment or uses in relation to skin diseases and/or skin disorders it is appreciated that the composition is used as an agent for topical application. Such an agent for topical application may be in the form of a gel, cream, lotion, ointment, shampoo, mask or similar forms, as exemplified in the examples.

In another aspect of the present invention the composition may be used as a cosmetic agent. It is appreciated that a cosmetic agent may be in the form of a gel, cream, lotion, ointment, shampoo, mask or similar forms, as exemplified in the examples.

In yet another aspect of the present invention the composition may be used as a moisturising agent. It is appreciated that a moisturising agent may be in the form of a gel, cream, lotion, ointment, shampoo, mask or similar forms, as exemplified in the examples. In a further aspect of the present invention the composition may be used as an anti-wrinkle agent. It is appreciated that an anti-wrinkle agent may be in the form of a gel, cream, lotion, ointment, shampoo, mask or similar forms, as exemplified in the examples.

In another aspect of the present invention the composition may be used as a moisturising agent. It is appreciated that a moisturising agent may be in the form of a gel, cream, lotion, ointment, shampoo, mask or similar forms, as exemplified in the examples.

The use of the composition of the present invention in the form of a shampoo is advantageous for alleviating the symptoms of skin diseases of the scalp. However, the shampoo may also be for cosmetic use.

In another aspect of the invention the composition has anti-wrinkle effect and found in the form of gel, cream, lotion, ointment, shampoo, mask or similar forms, as exemplified in the examples.

Examples of Specific Uses

Insect bites, for example mosquito bites, give rise to allergic reactions. The bite itches and swells. The composition of the present invention has shown a positive effect on the alleviation of the itching for up to 24 hours before re-appliance. The swelling declines within an hour.

Encountering allergic reactions from hogweed, the composition of the present invention reduce the burning and redness. The blisters that appear will disappear after 5 min. When repeating application of the composition of the present invention 3-5 times within 24 hours, the allergic reaction will disappear within a few days.

Damaged skin after excess exposure to sunlight will cause the skin to dry out and the collagen and elastic fibers are damaged. The composition of the present invention will provide the necessary moisture and nourishment to bring the skin back to a normal state and increase the amount of collagen and elastic fibers.

Scars, new as well as old scars, become less visible after using the composition of the present invention. The moisture and the cell nourishment will help the tissue to heal.

Contact with stinging nettle irritates the skin and cause it to burn. By applying the composition of the present invention the burning sensations are alleviated.

Alleviation of allergic reactions resulting from tinting of hair, use of perfume or allergic reactions occurring of other causes, show good results when using the composition of the present invention. The skin often itches and redness appears, occasionally also boils. Applying the composition of the present invention eliminate the redness and itching sensation. The boils heal after 5 days.

Heel chaps and chaps in hands are reduced when using the composition of the present invention on a daily basis.

Cellulite can be reduced by massaging the composition of the present invention on the involved area daily, resulting in the reappearance of firm and healthy skin.

As an acne/pimples treatment, the composition of the present invention has shown positive effects. The pimples reduce in size and numbers, and pus does not emerge. The scares after earlier acne become less visible.

Rosen/Erysipelas can be treated by using the composition of the present invention. Applying the composition on the affected areas twice a day will cause the symptoms to disappear after 7-9 days.

Penicillin side effects include severe skin rash, itching, and/or peeling. Using the composition of the present invention alleviates these symptoms.

The occurrence of fungus under hand nails and toe nails will cause the nails to become breakable and fragile. Use of the composition of the present invention will cause the fungus to disappear and help the nails to regain their strength.

Undefined rashes disappear after 5-7 days when using the composition of the present invention.

Rashes caused by Chickenpox and Scarlet fever are reduced by applying the composition of the present invention, and symptoms from the itching and inflamed sores are quickly alleviated.

Chronic rashes and rashes resulting from shaving disappear after using the composition of the present invention.

Symptoms caused by hand and foot eczemas are alleviated when using the composition of the present invention.

Relief of red baby bottom is achieved in a few days when using the composition of the present invention.

Herpes sores disappear when using the composition of the present invention. It also prevents the herpes from recurrence when using the composition on a regular basis. Stretch marks after pregnancy or slimming diet are also eliminated when using the composition of the present invention.

Dry skin achieves moisture when using the composition of the present invention.

Shinbone sores heal and the itching is alleviated when applying the composition of the present invention.

The composition of the present invention aids in the reduction of both size and number of wrinkles, resulting in an increase in the amount of collagen and elastin fibers in the skin.

The composition of the present invention will prevent infection of sores resulting from bite marks, and will cause them to heal after 7-10 days of application of the composition.

The composition of the present invention will also alleviate symptoms originating from rashes and/or sores in animals. Ear eczemas heal when using the composition of the present invention.

References

Averbeck M et al. (2007) Differential regulation of hyaluronan metabolism in the epidermal and dermal compartments of human skin by UVB irradiation. J Invest Dermatol 127:687-697.

Block, A., and Bettelheim, F.: Water Vapor Sorption of Hyaluronic Acid, Biochim Biophys. Acta 201, 69, 1970.

Campina, M B. V., Mallee, L. F. Hendrixx A., Cornelius, M. and Bronts, H. M. (WO/2001/065948) PROTEIN PREPARATION. Withdrawn, 2002.

Coo-Ranger, J. J., Zelisko, P. M., Brook, M. A (2004). Ionic silicone surfactants in water-in-oil silicone oil emusions conatining proteins Polymer Preprints 45:1, 674-75.

Davis J M, Murphy E A, Brown A S, Carmichael M D, Ghaffar A, Mayer E P. (2004) Effects of moderate exercise and oat beta-glucan on innate immune function and susceptibility to respiratory infection. Am J Physiol Regul Integr Comp Physiol.; 286(2):R366-72.

Davis J M, Murphy E A, Brown A S, Carmichael M D, Ghaffar A, Mayer E P. (2004) Effects of oat beta-glucan on innate immunity and infection after exercise stress. Med Sci Sports Exerc. 36(8):1321.

Everaerts F, Torrianni M, Hendriks M, Feijen, J. Biomechanical properties of carbodiimide crosslinked collagen: Influence of the formation of ester crosslinks. J Biomed Mater Res A. (2008) May; 85(2):547-55.

Goa K. L. and Benfield P. (1994). Hyaluronic Acid: A review of its Pharmacology and Use as a Surgical Aid in Ophtalmology and its Therapeutic Potential in Joint Disease and Wound Healing. Drugs 47: 536-566

Gu Y H., Takagi Y, Nakamura T, Hasegawa T, Suzuki I, Oshima M, Tawaraya H, Niwano Y. Enhancement of radioprotection and anti-tumor immunity by yeast-derived beta-glucan in mice. J Med. Food. 2005 Summer; 8(2):154-8

Huber C, Batchelor J R, Fuchs D, Hausen A, Lang A, Niederwieser D, Reibnegger G, Swetly P, Troppmair J, Wachter H. (1984). Immune response-associated production of neopterin. Release from macrophages primarily under control of interferon-gamma. J Exp Med 160:310-316.

Liu, H. (2007) Construction of Chitosan—Gelatin—Hyaluronic Acid Artificial Skin In Vitro Journal of Biomaterials Applications, 21:4, 413-430.

Mattson, G., E. Conklin, S. Desai, G. Nielander, M. D. Savage and S. Morgensen. (1993) A practical approach to crosslinking. Molecular Biology Reports 17: 167-183, Means, G. A., and Feeney, R. E. (1971). Chemical Modification of Proteins. Holden Day, Inc. San Francisco, Cambridge, London, Amsterdam.

Nakayama, G. R., Caton, M. C., Nova, M. P and Z Parandoosh (1997) Methods (Assessment of the Alamar Blue assay for cellular growth and viability in vitro Journal of Immunological Methods. 204: 2, 205-208.

Ozaki Y, Edelstein M P, Duch D S. (1988). Induction of indoleamine 2,3-dioxygenase: a mechanism of the antitumor activity of interferon-gamma. Proc Natl Acad Sci (USA) 85:1242-1246.

Pfefferkorn E R. (1986). Interferon-gamma blocks the growth of *Toxoplasma gondii* in human fibroblasts by inducing the host cells to degrade tryptophan. Proc Natl Acad Sci (USA) 81:908-912.

Pongjanyakul, T. and Puttipipatkhachorn, S. (2007) Xanthan-alginate composite gel beads: Molecular interaction and in vitro characterization International Journal of Pharmaceutics, 331, 1: 161-71.

Inventor: Rafkin U.S. Pat. No. 6,844,014 Jan. 18, 2005 Herbal healing lotion for veterinary use Reyad, M. and Paul, S. A. Solubility and Hydrolyzability of Films Produced by Transglutaminase Catalytic Crosslinking of Whey Protein'. Journal of Dairy Science Vol. 76, No. 1, 1993.

Schroecksnadel, K., Fischer, B., Schennach, H. Weiss, G., and D. Fuchs (2007) Antioxidants suppress TH1-type immune Response in vitro. Drug Metabolism Letters 1, 166-167.

Thalmann, C. R. and Lutzbeyer, T. (2002) Enzymatic crosslinking of proteins with tyrosinase. European Food Research and Technology, 214:4, 276-281.

WADSTEIN, Jan Publication date 16 May 2002, International application nr: WO/2002/038123 A SKIN CREAM COMPOSITION).

Wils, D. M., Fouchae, C., Labourse, S. (2005) Process for crosslinking proteins with a ketose containing 3-5 carbon atoms. USPAP 0130261

Winkler, C., Ueberall, F. And Fuchs, D. (2006) In vitro testing for Antiinflammatory Properties of compounds. Clinical Chemistry Letters, 6: 52, 1201-02.

Wireleitner, B. Neurauter, G., Schrøcknadel, K., Fuchs, D. (2003). Interferron gamma induced conversion of tryptophan.immunologic and neuropsychiatric aspects. Curr. med. Chem., 10:1581-1591.

Widner, B., Werner E R, Schennach H., Wachter H, Fuchs D. Simultaneous measurement of serum tryptophan and kynurenine by HPLC. Clin Chem (1997); 43:2424-6.

EXAMPLES

Example 1

Preparation of the composition of the present invention using EDC-NHS. 2.2 g of colostrum was dissolved in 100 ml of buffer. 0.1 g of hyaluronic acid was then dissolved in the already dissolved colostrum. For the conjugation of proteins and hyaluronic acid with EDC-NHS, buffers of concentration between 10-100 mM such as phosphate, HEPES or borate buffers are used. The conjugation reaction is typically performed between pH 6 and 8 and at either 4° C. to room temperature from 30 minutes to 120 minutes. The proteins in 48 hour colostrum 2.2 g and 0.1 g of hyaluronic acid individually was dissolved in 100 ml 10 mM sodium phosphate buffer, 400 mg of EDC and 1.1 g NHS was added to the 100 ml colostrum protein solution. After incubation preferably at room temperature, with stirring at 400-800 rpm, preferably 500 rpm. After 30-120 minutes, preferably 90 minutes, the bioconjugated proteins and hyaluronic acid were centrifuged at 30,000 g for 30 minutes, using Sorval centrifuge, SLA 1500 rotor. (The centrifugation step was repeated 3 times to remove unagglomerated protein and/or hydrocolloids.). The bioconjugated proteins with the hyaluronic add were then collected and incorporated in water-in-oil emulsion to give a cream with the properties described in the claims.

Example 2

Preparation of the composition of the present invention using glutaraldehyde (Means et al., 1971). Glutaraldehyde has been used in a variety of applications where maintenance of structural rigidity of protein is important. Phosphate buffers at pH 7.5 to 8.0 and HEPES buffers were used with a preference for sodium phosphate buffers, for glutaraldehyde treatment, reaction mixtures with 2.2 g of colostrum proteins was dissolved in 20 mM HEPES buffer (pH 7.5) in a total volume of 100 ml. 0.1 g of hyaluronic acid was then dissolved in the already dissolved colostrum. The solution was then treated with 5 ml of 2.3% freshly prepared solution of glutaraldehyde for 5-75 minutes, preferably 60 minutes at 15-37° C., preferably at room temperature. The reaction is terminated by addition of 10 µl of 1 M Tris-HCl, pH 8.0. After the reaction, the bioconjugated proteins and the hyaluronic acid were centrifuged at 30,000 g for 30 minutes, using Sorval centrifuge, SLA 1500 rotor. The centrifugation step was repeated 3 times to remove all traces of glutaraldehyde. The bioconjugated proteins with hyaluronic acid were then incorporated in water in oil emulsion to give a cream with the properties described in the above claims.

Example 3

Preparation of the composition of the present invention using calcium independent transglutaminase from Ajinomoto. 1-10 g of protein, preferably 2.2 g, was dissolved in 100 ml of buffers of concentration between 10-100 mM such as phosphate, HEPES or borate, preferably 10 mM phosphate buffer. 0.1 g of hyaluronic acid was then dissolved in the already dissolved colostrum. Between 1-200 units of transglutaminase, preferably 100 units were added to the reaction (Reyad and Paul, 1993). The reactions are typically performed between pH 6 and 8 and at either 4° C. to room temperature from 30 minutes to 4 hours, preferably 4 hours with stirring at 400-800 rpm at room temperature, preferably stirring at 400 rpm to avoid foaming of the protein. After 4 hours, the bioconjugated proteins with hyaluronic acid were centrifuged at 30,000 g for 30 minutes to collect the bioconjugated proteins with hyaluronic acid (the centrifugation step was repeated 3 times to remove unbioconjugated protein and hyaluronic acid) which were then incorporated in a cream which was a water-in-oil emulsion or an oil-in-water emulsion.

Example 4

Preparation of the composition of the present invention using tyrosinase (Thalmann and Lutzbeyer, 2002) from Sigma. The proteins (2.2 mg/ml of colostrum were dissolved in of 10 mM sodium phosphate buffer). 0.1 g of hyaluronic acid was then dissolved in the already dissolved colostrum. Different amounts of caffeic acid from 0-10 mM were solubilised in a mixture of ethanol and 10 mM sodium phosphate (2:5, w/w). Tyrosinase was dissolved in deionized water. For the agglomeration reaction, 4 ml of the freshly prepared protein solution were added to 500 µl of the caffeic acid solution, preferably 5 mM, and 500 µl of 10 mM sodium phosphate buffer respectively. The reaction was started by addition of 500 µl of the tyrosinase solution (100-500 U/ml), preferably a concentration of 330 U/ml. After an incubation time of 1-12 hours, preferably an incubation time of 3 hours, with stirring between 400-700 rpm, 500 μl of a buffer were added [8 ml water, 2 ml Tris-(hydroxymethyl)-aminomethane/HCL (0.5 M, pH 6.8), 1.6 ml glycerine, 0.8 ml mercaptoethanol, 0.4 ml bromophenol blue (0.05%), 0.25 g SDS]. For reference experiments, samples were prepared by replacing the tyrosinase solution in the reaction mixture with water (12). After the agglomeration reaction, the bioconjugated proteins with hyaluronic acid were centrifuged at 30,000 g for 30 minutes to collect the bioconjugated proteins with hyaluronic acid which were then incorporated in a cream which was a water-in-oil emulsion. The centrifugation step was repeated 3 times to remove non-bioconjugated protein and hyaluronic acid before being incorporated in the cream.

Example 5

Preparation of the composition of the present invention using Dihydroxyacetone (DHA). The proteins (1.5 mg/ml of colostrum were dissolved in of 10 mM sodium phosphate buffer). 0.1 g of hyaluronic acid was then dissolved in the already dissolved colostrum. Between 10-30% w/w with respect to protein concentration of DHA was then added to start the reaction (14). The preferable concentration of DHA to be used is around 20%. After an incubation time of 60-180 minutes, preferably an incubation time of 90 minutes with stirring between 400-700 rpm, the bioconjugated proteins with hyaluronic acid were centrifuged at 30,000 g for 30 minutes to collect the bioconjugated proteins with hyaluronic acid (The centrifugation step was repeated 3 times to remove unbioconjugated protein and hyaluronic acid which were then incorporated in a cream which was a water-in-oil emulsion.

Example 6

Preparation of the composition of the present invention using aryl azides. Aryl azides are crosslinking photoreactive groups reagents are aryl azides When an aryl azide is exposed to UV-light, it forms a nitrene group that can initiate addition reactions with double bonds, insertion into CH and N—H sites, or subsequent ring expansion to react as a nucleophile with primary amines.

Examples of aryl azides include Phenyl Azide Hydroxyphenyl Azide Nitrophenyl Azide, Tetrafluorophenyl Azide.

In experimental laboratory conditions colostrum (2.2 mg/ml) was dissolved in 10 mM phosphate buffer and mixed together with the phenyl azide (100 mM) in an eppendorf tube and exposed to uv light between 254 and 366 nm for 30 mins. This resulted in the soluble proteins becoming bioconjugate and hence insoluble. The eppendorf tube was then centrifuged at 14,000 rpm/30 mins in an eppendorf centrifuge to harvest the bioconjugated proteins.

Example 7

Small Scale Production of Nanoparticles
a. 2.2 g of colostrum powder was stirred with 70 ml of 10 mM phosphate buffer, pH 7.4 for 60 minutes at room temperature.
b. 0.1 g of hyaluronic acid (Hyacare, Novozymes) was dissolved by stirring slowly heating in 25 ml 10 mM phosphate buffer, pH 7.4 and mixed with the above dissolved colostrum.
c. 400 mg of DHA was dissolved in 5 ml of 10 mM phosphate buffer, pH 7.4 and then mixed with the dissolved colostrum and hyaluronic acid and stirred at 600 rpm for 90 minutes.

The reaction was conducted at different temperatures, 5° C., 10° C., 15° C. and room temperature. Best results were obtained with 15° C. and room temperature (FIG. 1A, 1B).
d. The above suspension was then centrifuged using a Sorvall high speed centrifuge at 30,000 g for 40 minutes to settle the colostrum nanoparticles which were then collected and used in the cream formulation.

In order to visualize the nanoparticles, a droplet of the bioconjugated colostrum was mounted and subjected to atomic force microscopy using a Light Lever AFM Scanner (Model no. P-01-0005-0) from Pacific Nanotechnology (FIG. 1).

Determination of the Amount of Bioconjugated Colostrum
a1. Whole colostrum powder is dissolved in phosphate buffer and the total protein concentration is measured using the BioRad protein assay.
b1. After production of the bioconjugated nanoparticles as described above, the total protein concentration in the supernatant of the centrifuged sample is measured using the BioRad protein assay.
c1. The amount of bioconjugated colostrum is then calculated as the difference between the protein concentration measured in step a1 above and the protein concentration measured in step b1 above.

Example 8

Components of Colostrum (Fresh, Frozen or Dried Colostrums Between 0-72 h Milking).

In order for the composition of the present invention to be effective, the colostrum should comprise the following components:
  a. Lactoferrin in a concentration between 10-50 μg/ml of bioconjugated proteins, preferably around 35 μg.
  b. Beta-lactoglobulin in a concentration of 2000-3000 ng/ml of bioconjugated protein, preferably 2300 ng/ml.
  c. Alpha-lactalbumin in a concentration of 2000-3000 ng/ml of bioconjugated protein, preferably 2200 ng/ml.
  d. IgG in a concentration of 3-8 mg/ml of bioconjugated protein, preferably 4 mg/ml of bioconjugated protein,
  e. IgA in a concentration of 0.08-2.00 mg/ml bioconjugated protein, preferably 0.15 mg/ml of bioconjugated protein.
  f. IgM concentration of 1-3 mg/ml, preferably 1 mg/ml of bioconjugated protein
  g. IGF-1 in a concentration of 2-10 ng/ml bioconjugated protein, preferably 5 ng/ml of bioconjugated protein.

Example 9

Figure 2:
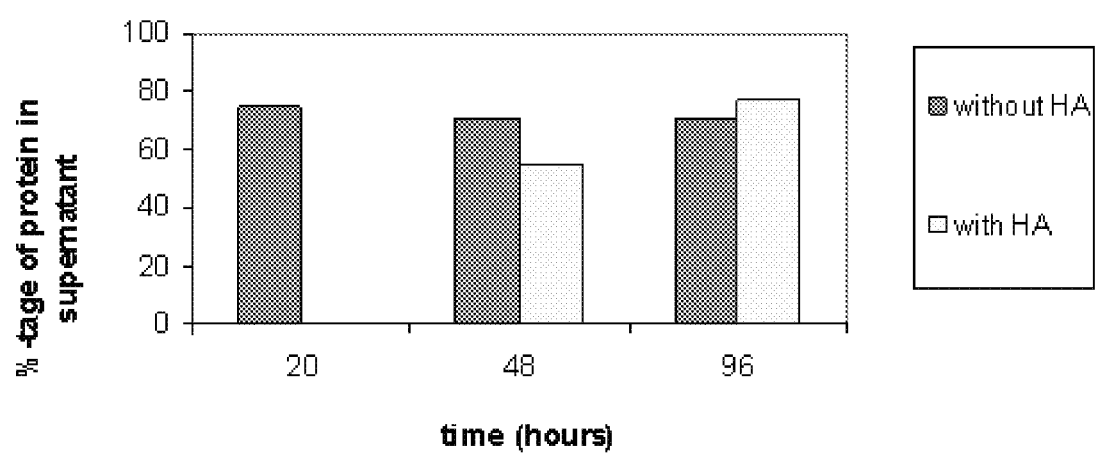
FIG. 2. Stability of low lactose colostrum bioconjugates with and without hyaluronic acid against acid protease.

Protease treatment protocol of the low lactose colostrum bioconjugates with and without the hydrocolloids. The bioconjugates were dispersed in buffer of pH 5.6 and to the dispersion was added the acid protease. The reaction mixtures were incubated at 25° C. with shaking at 150 rpm for 4 days. Aliquots of the mixtures at 20, 48 and 96 hours were then taken and heated at 80° C. for 5 minutes to inactivate the protease. The mixture was then centrifuged at 15,000 rpm to obtain the pellet containing the bioconjugates. The supernatant contained the protein hydrolysed from the bioconjugates by the protease. The Protein assay (BioRad) on the supernatants after protease treatment and the original bioconjugates dispersion gives a picture of the action of protease on the bioconjugates and the stability of the bioconjugated particles against protease action (FIG. 2.). The proteins conjugated together with the hydrocolloids are much more stable against proteolytic activity as compared to the proteins conjugated with the hydrocolloid (FIG. 2)

Examples 10-13

In the following examples the component "Colostrum serum agent" is the bioconjugated colostrum and hydrocolloid, wherein the hydrocolloid is hyaluronic acid.

Example 10

| INGREDIENTS - SKIN GEL | AMOUNT (% w/w) |
|---|---|
| Water | 67.442 |
| Colostrum serum agent | 19.4 |
| Phenoxyethanol | 1.116 |
| Ethylhexylglycerin | 0.124 |
| Citric acid | 0.145 |
| Sodium hyaluronate | 0.1 |
| Aloe Barbadensis Leaf Juice | 9.925 |
| Tetrasodium iminodisuccinate | 0.068 |
| Xanthan gum | 1.5 |
| Potassium sorbate | 0.005 |
| Sodium sulfite | 0.005 |
| Sodium benzoate | 0.02 |
| Sodium dehydroacetate | 0.15 |

Example 11

| INGREDIENTS - LIP LOTION | AMOUNT (% w/w) |
|---|---|
| Water | 59.7 |
| Colostrum serum agent | 6.79 |
| Sodium benzoate | 0.4 |
| Cetearyl olivate, sorbitan olivate | 4 |
| Oliwax | 3 |
| Butyrospermum parkii | 10 |
| Simmondsia chinensis oil | 10 |
| Cera alba | 4 |
| Tocopherol | 0.2 |
| Ammunium acylodimethylaurate | 1 |
| Citric acid | 0.18 |
| Ethylhexylglycerine | 0.045 |
| Phenoxyethanol | 0.675 |
| Sodium hyaluronate | 0.01 |

Example 12

| INGREDIENTS - SKIN LOTION | AMOUNT (% w/w) |
|---|---|
| Aqua | 56.207 |
| Sodium cocoyl glutamate | 4.5 |
| Colostrum serum agent | 14.55 |
| Phenoxyethanol | 0.99 |
| Ethylhexylglycerin | 0.11 |
| Butyrospermum parkii | 7.5 |
| Simmondsia chinensis seed oil | 7.5 |
| Prunus amygdalus dulcis oil | 5.0 |
| Acrylates/c10-30 alkyl acrylate crosspolymer | 1.0 |
| Sodium benzoate | 0.4 |
| Xanthan gum | 0.5 |
| Tetrasodium iminodisuccinate | 0.068 |
| Tocopherol | 0.201 |

-continued

| INGREDIENTS - SKIN LOTION | AMOUNT (% w/w) |
|---|---|
| Retinyl palmitate | 0.0555 |
| Arachis hypogaea oil | 0.0435 |
| Citric acid | 0.7 |
| Sodium chloride | 0.675 |

Example 13

| INGREDIENTS - SKIN CREAM | AMOUNT (% w/w) |
|---|---|
| Aqua | 42.8 |
| Prunus Amygdalus Dulcis Oil | 15.0 |
| Colostrum Serum | 14.45 |
| Butyrospermum Parkii Butter | 10.0 |
| Aloe Barbadensis | 9.925 |
| Cetyl PEG/PPG-10/1 Dimethicone | 3.0 |
| Cera Alba | 2.0 |
| Tocopherol | 1.0 |
| Citric Acid Citric Acid | 0.045 |
| Ethylhexylglycerin | 0.045 |
| Sodium Chloride | 0.5 |
| Phenoxyethanol | 0.905 |
| Potassium Sorbate | 0.005 |
| Sodium Benzoate | 0.22 |
| Sodium Sulfite | 0.005 |
| Sodium Hyaluronate | 0.1 |

Example 14

Immunostimulatory and anti-inflammatory effect. The model system using activates PBMCs has been well established in clinical immunology and allows for standardization of T-cell activation and T-cell/macrophage interaction (1). Mitogen PHA significantly increases tryptophan degradation in human PBMCs. Upon co-incubation of cells with colostrum ingredients this activity is suppressed dose-dependently. This biochemical immunobiochemical pathway was demonstrated earlier (4) to be stimulated in activated PBMC by Th1-type cytokine IFN-gamma released from stimulated T cells.

14a. Cell Culture:

Human peripheral blood mononuclear cells (PBMCs) freshly obtained from whole blood of healthy donors were isolated by density centrifugation (Lymphoprep, Nycomed Pharma AS, Oslo, Norway) and maintained in RPMI 1640 (PAA Laboratories, Linz, Austria) supplemented with 10% heat-inactivated fetal calf serum (Gibco, Invitrogen, Austria), 2 mM I-glutamine (Serve, Heidelberg, Germany) and 50 µg/ml gentamycin (Bio-Whittaker, Walkersville, Md.) and stimulated them with mitogens (1). PBMCs were seeded at a density of $1.5 \times 10^6$ cells $mL^{-1}$ and preincubated with colostrum components for 30 min before stimulation with phytohemagglutinin (PHA). The mitogen concentration of 10 µg/mL was optimal for detecting suppressive effects of compounds. Cells were incubated for 48 h at 37° C. and 5% $CO_2$, and supernatants were collected thereafter.

Measurements of neopterin formation by methods such as ELISA and/or tryptophan degradation by HPLC were used as convenient readouts; where both biochemical effects are induced by interferon-gamma in human macrophages (2).

14b. Activation of PBMC

PBMC were seeded at a density of $3 \times 10^6$ $ml^{-1}$ in completed culture medium and exposed to colostrum preparations with and without the preservative euxyl PE9010 concentrations ranging from 30-40 mg/ml and diluted from 5 to 500 times. To test the effect of colostrum preparations on activated lymphocytes, PBMC were co-incubated with colostrum preparations and the mitogen phytohaemagglutinin (PHA, Sigma). After 48 h incubation, culture supernatants were harvested by centrifugation and frozen at −20° C. until measurement. All experiments were performed in four independent experiments with PBMC in two to three parallels.

14c. Measurement.

Concentrations of tryptophan and the degradation product kynurenine in culture supernatants were measured by high performance liquid chromatography (HPLC), using 3-nitro-1-tyrosine as external standard [3]. By calculating the ratio of kynurenine versus tryptophan concentrations (=kyn/trp) the activity of the enzyme IDO is estimated. Production of neopterin was determined by ELISA (BRAHMS, Berlin, Germany) according to the manufacturer's instructions with a detection limit of 2 nM.

14d. Cell Viability

To control cell viability, PBMC were harvested after centrifugation and stained with the DNA-probe propidium iodide. This stain only crosses the membrane of necrotic cells, highlighting the DNA of these cells. Analysis was performed on a fluorescence-activated cell sorter (Coulter Epics XLMCL, Beckman-Coulter).

14e. Statistical Analysis

Statistical analysis was performed using the Mann-Whitney U-test. The p-values below 0.05 were considered to indicate significant differences Results The results are summarized in FIGS. 11-18.

Collection of all Results Including Statistics

The above graphs include data on unstimulated cells and stimulated cells. Statistics always compare with the corresponding control, neopterin, kynurenine and kyn/trp and are given as percent change of baseline (stimulated or unstimulated controls). Tryptophan results are given as percent change of tryptophan present in the culture medium supplied. There are at least two interesting findings:

1. In PHA stimulated cells, the colostrum preparation without the preservative suppresses mitogen-induced tryptophan degradation (interestingly no such effect on neopterin production) in a dose-dependent way (FIG. 11).
Euxyl has a stronger effect and when euxyl is added to colostrum the suppressive effect also becomes stronger (FIG. 11) and is also active to suppress neopterin production (FIG. 13).
In summary, this shows an anti-inflammatory effect on the Th1-axis of immune response.
2. In the unstimulated cells, colostrum has a stimulatory effect on neopterin production (FIG. 14) and on tryptophan degradation (FIG. 12), whereas euxyl still has an inhibitory effect (FIG. 12) (like in stimulated cells—there is always some minor but detectable baseline activity of the enzymes involved). This may explain that the addition of euxyl to colostrum counteracts the effec of pure colostrum on neopterin production (FIG. 14) and on tryptophan degradation (FIG. 12). In part it is an even greater surprise to see that the higher dilution of colostrum seems to have a stronger effect especially on tryptophan degradation in unstimulated cells (FIG. 12).

Conclusions

It has been demonstrated in this study that the colostrum ingredients act prostimulatory (stimulate neopterin production) on resting unstimulated PBMCs, which may correspond to the antiviral/antitumoral properties of the extract.

With the above studies it has been proven that the colostrum ingredients of the cream in vitro show both anti-inflammatory effect in PBMC cells stimulated with PHA as well as show immunostimulatory effect on resting immune system.

It has also been demonstrated the effect of the colostrum cream in vivo on the skin of several subjects suffering from eczema and psoriasis, immune related diseases as seen from the pictures of patients before and after use of the colostrum cream.

Example 15

Cell proliferation. Cell proliferation assays were performed using well established methods (2) using Alamar blue (Invitrogen, Paisley, UK) as per manufacturers instructions measuring the change in absorbance. For the proliferation assays, the human colonic carcinoma cell line HT29 cells were used. Cell viability, determined by the ability to exclude 0.2% trypan blue, was greater than 90% in all experiments.

Study Protocol

Briefly, cells were seeded at 2000 cells/well and grown in DMEM containing glutamine and 10% foetal calf serum in 96 well plates overnight. The following day, cells were washed with DMEM alone and incubated with 1, 5 or 10 mg/ml colostrum protein (v/v) preparation with or without Euxyl or with 1%, 0.3% or 0.06% Euxyl (concentrations equivalent to those found in the samples containing Euxyl) and incubated under serum starved conditions for 24 hours. Cells incubated in DMEM+10% FCS were used as a positive control whereas cells incubated in DMEM alone were used as a negative control. The following day Alamar blue was added to each well and change in absorbance at 570 nm was determined after 3-5 hours.

At the two lower doses (1 and 5 mg/ml) tested all three colostrums samples (containing Euxyl) stimulated proliferation in HT29 cells. This effect was not just due to the Euxyl but was predominantly caused by the colostrum.

Example 16

Modulation of immune activation cascades. The aim of this study was to assess the impact of different bioconjugated BC nanoparticle preparations of the present invention on Th-1 type immune response in terms of tryptophan degradation and formation of neopterin in unstimulated and phytohaemagglutinin (PHA)-stimulated human PBMC. The results were compared with the effects of lactoferrin and the globally accepted cosmetic preservative Euxyl 9010, which was used in a topical cream to preserve the colostrum ingredients.

Isolation and Stimulation of Human PBMC

PBMC were isolated from whole blood obtained from healthy donors, of whom informed consent was obtained that their donated blood unit was used for scientific purposes if not otherwise used. Separation of blood cells was performed using density centrifugation (Lymphoprep, Nycomed Pharma AS, Oslo, Norway). After isolation, PBMC were washed three times in phosphate buffered saline containing 0.2% EDTA [0.5 mmol/L]. Cells were maintained in RPMI 1640 supplemented with 10% heat-inactivated fetal calf serum (Biochrom, Berlin, Germany), 1% of 200 mmol/L glutamine (Serve, Heidelberg, Germany) and 0.1% of gentamicin (50 mg/ml, Bio-Whittaker, Walkersville, Md.) in a humidified atmosphere containing 5% $CO_2$ for 48 h. This procedure was observed earlier to reveal best reproducible results when applied for testing of anti-inflammatory effects of compounds or drugs (Widner et al., 1997). Average tryptophan content in the supplemented RPMI 1640 medium was 31.5 μmol/L. For each of the three experiments run in duplicates, PBMC were freshly prepared. Isolated PBMC were plated at a density of $1.5\times10^6$ cells/ml in supplemented RPMI 1640, preincubated for 30 minutes with or without BC preparations and stimulated or not with 10 μg/ml PHA for 48 h.

Measurement of Tryptophan, Kynurenine, and Neopterin Concentrations

After incubation of cells for 48 h, supernatants were harvested by centrifugation and tryptophan and kynurenine concentrations were measured by high performance liquid chromatography (HPLC) using 3-nitro-L-tyrosine as internal standard (Widner and others 1997). To estimate IDO activity, the kynurenine to tryptophan ratio (kyn/trp) was calculated and expressed as μmol kynurenine/mmol tryptophan (Widner et al., 1997). Neopterin concentrations were determined by ELISA (BRAHMS, Hennigsdorf/Berlin, Germany) according to the manufacturer's instructions with a detection limit of 2 nmol/L.

Measurement of Cell Viability

After incubation of PBMC and THP-1 cells, cell viability was measured by MTT-test (3-[4,5-dimethyldiazol-2-yl]-2,5 diphenyl tetrazolium bromide; Sigma, Vienna, Austria) and by trypan blue exclusion method in three experiments done in triplicates. No toxicity could be observed at the concentration range applied (data not shown).

Statistical Analysis

For statistical analysis, the Statistical Package for the Social Sciences (version 14 SPSS, Chicago, Ill., USA) was used. Because not all data sets showed normal distribution, for comparison of grouped data non-parametric Friedman test and Wilcoxon signed ranks test were applied. P-values below 0.05 were considered to indicate significant differences.

Results

The results of Example 16 is described below and summarized in FIGS. 19-23.

Effect of Bovine Colostrum (BC) Preparations on Tryptophan Metabolism and Neopterin Formation in Unstimulated Human Peripheral Blood Mononuclear Cells (PBMC)

The supernatants of unstimulated PBMC, cultivated for 48 h under standard cultivation conditions, contained 30.4±1.9 μmol/L tryptophan and 0.9±0.16 μmol/L kynurenine resulting in a kynurenine to tryptophan ratio (kyn/trp) of 28.1±3.6 μmol/mmol, as a measure of spontaneous IDO activity. In the same supernatants, neopterin concentrations of 3.6±0.4 nmol/L were detected (FIG. 19).

Treatment of PBMC with 0.2 mg/ml BC, containing low amounts of lactose, enhanced IDO activity about two-fold (199.7±29.2%), whereas a significant reduction of IDO activity to 72.2±5.9% could be observed at a dosage of 20 mg/ml. BC with higher amounts of lactose did not influence tryptophan metabolism significantly and application of lactoferrin alone suppressed indoleamine 2,3-dioxygenase (IDO) activity not until a dosage of 20 mg/ml (54.7±5.0%; FIG. 20A). Regarding neopterin formation, BC with low amounts of lactose beared the strongest capacity to induce neopterin formation at doses of 0.2 mg/ml (258.5±30.0%) and BC with high amounts of lactose induced a comparable enhancement of neopterin formation at 2 mg/ml to 235±22.3%. Lactoferrin induced only a moderate increase of neopterin at 0.2 or 2 mg/ml to 125±2.8% or 132±4.1%, respectively (FIG. 20B).

Another low lactose colostrum preparation, strongly induced IDO activity at 2 mg/ml to 1122.0±356%, which was lowered by the addition of the preservative euxyl to 296.6±70.3% (FIG. 21A). Treatment of PBMC with euxyl alone suppressed spontaneous IDO activity to 67.9±6.3% or 42.3±4.75% at doses of 2 and 20 mg/ml, respectively. Neopterin levels also increased strongest after treatment of cells with colostrum containing no euxyl (2 mg/ml: 196±21.2%; 20 mg/ml: 209±26.9%), which was reduced by the addition of euxyl to 128±12.7% and 169±21.6% at 2 and 20 mg/ml, respectively. Application of euxyl alone suppressed neopterin formation at doses of 2 mg/ml to 90.4±4.1% and at 20 mg/l to 76.1±1.6% (FIG. 21B).

Effect of BC Preparations on Tryptophan Metabolism and Neopterin Formation in PHA-Stimulated PBMC Upon treatment of PBMC with phytohemagglutinin (PHA) [10 μg/ml] for 48 h, tryptophan content in the supernatant decreased to 8.2±2.0 μmol/L whereas kynurenine concentrations increased concomitantly to 9.8±1.3 μmol/L, indicating an approximately 47-fold increase of IDO activity (Kyn/trp: 1312±459 μmol/mmol). Within the same supernatants neopterin concentrations raised about 3.6-fold to a level of 13.2±3.6 nmol/L (FIG. 19).

Pre-treatment of PHA-stimulated PBMC cultures with BC preparations containing low or high amounts of lactose or lactoferrin alone, revealed a strong and dose dependent capacity to suppress PHA-induced tryptophan degradation. BC with low amounts of lactose showed the strongest inhibitory effect on IDO enzyme activity (0.2 mg/ml: 25.4±5.3%) followed by the effect of lactoferrin (0.2 mg/ml: 34.0±9.7%) and BC with higher amounts of lactose (46.0±16.6%). At higher concentrations of 2 or 20 mg/ml all preparations almost completely counteracted PHA-stimulated tryptophan degradation in the same rank order of activity (FIG. 22A). Mitogen induced neopterin formation was also diminished by these BC preparations and lactoferrin, although with lower potency as compared to the effects on tryptophan degradation (FIG. 22B). Again, BC with higher amounts of lactose showed the weakest inhibitory effect on PHA-stimulated neopterin formation, exerting a significant inhibition to 70.5±7.2% only at a dosage of 20 mg/ml. The potency of BC with low amounts of lactose, taking effect at 2 mg/ml (64.0±4.8%) and 20 mg/ml (37.1±3.0%), were comparable to the effect of lactoferrin (2 mg/ml: 61.3±11.7%; 20 mg/ml: 31.1±3.9%).

The second BC preparation (low lactose) showed a lower capacity to counteract PHA-induced tryptophan degradation and neopterin formation in PBMC. Pre-treatment of cells with BC containing no euxyl suppressed PHA-stimulated IDO activity at 2 mg/ml to 78.2±5.0% and to 28.9±6.4% at 20 mg/ml, which was slightly enhanced by the addition of euxyl to 74.1±11.9 and 17.7±6.1%, respectively. Euxyl alone suppressed PHA-stimulated tryptophan degradation at doses of 2 mg/l to 60.1±11.0% and almost completely at 20 mg/ml to 2.9±0.4% (FIG. 23A). Interestingly, this BC preparation did not affect PHA-induced neopterin formation. A significant reduction of PHA-stimulated neopterin formation with BC containing euxyl, at a dosage of 20 mg/ml to 73.0±5.7%, may possibly be linked to the suppressing capacity of euxyl (2 mg/ml: 85.4±3.5%; 20 mg/ml: 34.2±4.2%; FIG. 23B).

The invention claimed is:

1. A nanoparticle composition comprising colostrum, which comprises IgA, IgM, and lactoferin, and at least one hydrocolloid selected from the group consisting of: agar, starch, potato starch, carrageenan, guar gum, pectin, xanthan gum, alginate, sodium alginate, arabinoxylan, cellulose, carboxymethyl cellulose, chitin, xylan, curdlan, beta-glucan, gum Arabic, locust bean gum, hyaluronic acid, gelatin and soya protein, wherein said colostrum, which comprises IgA, IgM, and lactoferin, and said hydrocolloid are covalently linked so as to produce said nanoparticle composition.

2. The nanoparticle composition according to claim 1, wherein the at least one hydrocolloid is selected from the group consisting of: guar gum, pectin, xanthan gum, alginate, arabinoxylan, cellulose, carboxymethyl cellulose, chitin, xylan, beta-glucan, gum Arabic, hyaluronic acid, and gelatin.

3. The nanoparticle composition according to claim 1, wherein said nanoparticle composition has a diameter in the range of 10 nm-300 nm.

4. The nanoparticle composition according to claim 1, wherein the amount of said colostrum is in the range of 1%-95% w/w of the total composition.

5. The nanoparticle composition according to claim 1, wherein the amount of said at least one hydrocolloid is in the range of 0.01-20% w/w of the total amount of colostrum.

6. A pharmaceutical composition comprising a pharmaceutically effective amount of the composition of claim 1.

7. The pharmaceutical composition according to claim 6, further comprising a pharmaceutical or a physiologically acceptable carrier.

8. The pharmaceutical composition according to claim 6, wherein said pharmaceutical is formulated for treating skin diseases and/or skin conditions, wherein said skin disease and/or skin condition is selected from the group consisting of eczemas of unknown aetiology, rashes, itchy skin, irritated redness, atopic dermatitis, psoriasis, wounds, postoperative wounds, sores, diabetic sores, skin conditions caused by bacteria, skin conditions caused by viruses, skin conditions caused by fungus, skin conditions caused by insects, skin conditions caused by plants, acne, herpes, pruritus and bed sores.

9. A method of making the nanoparticle composition of claim 1 comprising:
    a) providing colostrum, which comprises IgA, IgM, and lactoferin;
    b) providing at least one hydrocolloid selected from the group consisting of: agar, starch, potato starch, carrageenan, guar gum, pectin, xanthan gum, alginate, sodium alginate, arabinoxylan, cellulose, carboxymethyl cellulose, chitin, xylan, curdlan, beta-glucan, gum Arabic, locust bean gum, hyaluronic acid, gelatin and soya protein;
    c) mixing said colostrum and said at least one hydrocolloid;
    d) providing at least one cross-linking agent; and
    e) mixing said colostrum, said at least one hydrocolloid, and said at least one cross-linking agent so as to obtain said nanoparticle composition.

10. The method according to claim 9, wherein said cross-linking agent of step d) is selected from the group consisting of: EDC/NHS or derivatives thereof, glutaraldehyde or derivatives thereof, transglutaminase or derivatives thereof, tyrosinase or derivatives thereof, and dihydroxyacetone or derivatives thereof.

11. A method of using the composition of claim 1 as a cosmetic, anti-wrinkle agent, or moisturizing agent comprising:
    a) providing the composition of claim 1; and
    b) applying said composition to a region of skin of a subject so as to improve cosmetic appearance, reduce wrinkles, or moisturize the region of skin of said subject.

12. A method of inhibiting a skin disease or skin condition comprising:
    a) providing the composition of claim 1; and
    b) applying a therapeutically effective amount of said composition to a region of skin of a subject having a skin disease or skin condition, whereby said skin disease or skin condition is inhibited after application of said composition.

13. The method of claim 12, wherein said skin disease or skin condition is selected from the group consisting of itchy skin, wounds, sores, atopic dermatitis, and psoriasis.

14. The nanoparticle composition according to claim 1, wherein said colostrum or part hereof that is covalently linked to said hydrocolloid comprises IgA, IgM, IgG, and Lactoferrin of colostrum.

15. The nanoparticle composition according to claim 1, wherein said colostrum that is covalently linked to said hydrocolloid comprises IgA, IgM, IgG, Lactoferrin, and beta-lactoglobulin of colostrum.

16. The nanoparticle composition according to claim 1, wherein said said colostrum that is covalently linked to said hydrocolloid comprises IgA, IgM, IgG, Lactoferrin, beta-lactoglobulin, and alpha-lactalbumin of colostrum.

17. The nanoparticle composition according to claim 1, wherein said said colostrum that is covalently linked to said hydrocolloid comprises IgA, IgM, IgG, Lactoferrin, beta-lactoglobulin, alpha-lactalbumin, and IGF-1 of colostrum.

18. A nanoparticle composition comprising whole colostrum and at least one hydrocolloid selected from the group consisting of: agar, starch, potato starch, carrageenan, guar gum, pectin, xanthan gum, alginate, sodium alginate, arabinoxylan, cellulose, carboxymethyl cellulose, chitin, xylan, curdlan, beta-glucan, gum Arabic, locust bean gum, hyaluronic acid, gelatin and soya protein, wherein said whole colostrum and said hydrocolloid are covalently-linked so as to produce said nanoparticle composition.

19. The nanoparticle composition according to claim 18, wherein the at least one hydrocolloid is selected from the group consisting of: guar gum, pectin, xanthan gum, alginate, arabinoxylan, cellulose, carboxymethyl cellulose, chitin, xylan, beta-glucan, gum Arabic, hyaluronic acid, and gelatin.

20. The nanoparticle composition according to claim 18, wherein said nanoparticle composition comprises a diameter in the range of 10nm-300 nm.

21. The nanoparticle composition according to claim 18, wherein the amount of said at least one hydrocolloid is in the range of 0.01-20% w/w of the total amount of whole colostrum.

22. The nanoparticle composition according to claim 1, wherein said colostrum that is covalently linked to said hydrocolloid comprises:
    a. Lactoferrin in a concentration between 1-100 μg/ml,
    b. beta-lactoglobulin in a concentration between 1000-4000 ng/ml,
    c. alpha-lactalbumin in a concentration between 1000-4000 ng/ml,
    d. IgG in a concentration between 1-10 mg/ml,
    e. IgA in a concentration between 0.05-3.00 mg/ml,
    f. IgM in a concentration between 0.05-4.00 mg/ml, and
    g. IGF-1 in a concentration between 1-15 ng/ml.

23. The nanoparticle composition according to claim 1, wherein said colostrum that is covalently linked to said hydrocolloid comprises:
    a. Lactoferrin in a concentration between 10-50 μg/ml,
    b. beta-lactoglobulin in a concentration between 2000-3000 ng/ml,
    c. alpha-lactalbumin in a concentration between 2000-3000 ng/ml,
    d. IgG in a concentration between 3-8 mg/ml,
    e. IgA in a concentration between 0.08-2.00 mg/ml,
    f. IgM in a concentration between 1-3 mg/ml, and
    g. IGF-1 in a concentration between 2-12 ng/ml.

24. The nanoparticle composition according to claim 1, wherein said colostrum that is covalently linked to said hydrocolloid comprises:
    a. Lactoferrin in a concentration of at least 35 µg/ml,
    b. beta-lactoglobulin in a concentration of at least 2300 ng/ml,
    c. alpha-lactalbumin in a concentration of at least 2200 ng/ml,
    d. IgG in a concentration of at least 4 mg/ml,
    e. IgA in a concentration of at least 0.15 mg/ml,
    f. IgM in a concentration of at least 1 mg/ml, and
    g. IGF-1 in a concentration of at least 5 ng/ml.

25. A nanoparticle composition comprising colostrum, which comprises IgA, IgM, and lactoferin, and at least one hydrocolloid selected from the group consisting of: agar, starch, potato starch, carrageenan, guar gum, pectin, xanthan gum, alginate, sodium alginate, arabinoxylan, cellulose, carboxymethyl cellulose, chitin, xylan, curdlan, beta-glucan, gum Arabic, locust bean gum, hyaluronic acid, gelatin and soya protein, wherein said colostrum and said at least one hydrocolloid are covalently linked so as to produce said nanoparticle composition, wherein fats and/or lactose is removed from the colostrum.

\* \* \* \* \*